(12) United States Patent
Radtke et al.

(10) Patent No.: US 11,596,342 B2
(45) Date of Patent: Mar. 7, 2023

(54) AUTOMATIC DETECTION OF BODY PLANES OF ROTATION

(71) Applicant: Medtronic, Inc., Minneapolis, MN (US)

(72) Inventors: Andrew Radtke, Minneapolis, MN (US); Tarek D. Haddad, Minneapolis, MN (US); Michelle M. Galarneau, Minneapolis, MN (US); Vinod Sharma, Maple Grove, MN (US); Jeffrey D. Wilkinson, Vadnais Heights, MN (US); Brian B. Lee, Golden Valley, MN (US); Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 312 days.

(21) Appl. No.: 16/909,778

(22) Filed: Jun. 23, 2020

(65) Prior Publication Data

US 2021/0085202 A1 Mar. 25, 2021

Related U.S. Application Data

(60) Provisional application No. 62/902,751, filed on Sep. 19, 2019.

(51) Int. Cl.
*A61B 5/341* (2021.01)
*A61B 5/11* (2006.01)
(Continued)

(52) U.S. Cl.
CPC ............ *A61B 5/341* (2021.01); *A61B 5/0031* (2013.01); *A61B 5/02156* (2013.01);
(Continued)

(58) Field of Classification Search
CPC .......... A61B 2562/0219; A61B 5/0031; A61B 5/02156; A61B 5/02158; A61B 5/1114;
(Continued)

(56) References Cited

U.S. PATENT DOCUMENTS 6,044,297 A 3/2000 Sheldon et al.
7,471,290 B2 12/2008 Wang et al.
(Continued)

FOREIGN PATENT DOCUMENTS

EP 0762908 B1 5/2003
EP 1115350 B1 8/2003
(Continued)

OTHER PUBLICATIONS

International Search Report and Written Opinion of International Application No. PCT/US2020/040084, dated Sep. 23, 2020, 12 pp.
(Continued)

*Primary Examiner* — Ankit D Tejani
(74) *Attorney, Agent, or Firm* — Shumaker & Sieffert, P.A.

(57) ABSTRACT

Techniques are disclosed for automatically calibrating a reference orientation of an implantable medical device (IMD) within a patient. In one example, sensors of an IMD sense a plurality of orientation vectors of the IMD with respect to a gravitational field. Processing circuitry of the IMD processes the plurality of orientation vectors to identify an upright vector that corresponds to an upright posture of the patient. The processing circuitry classifies the plurality of orientation vectors with respect to the upright vector to define a sagittal plane of the patient and a transverse plane of the patient. The processing circuitry determines, based on the upright vector, the sagittal plane, and the transverse plane, a reference orientation of the IMD within the patient. As the orientation of the IMD within the patient changes
(Continued)

over time, the processing circuitry may recalibrate its reference orientation and accurately detect a posture of the patient.

23 Claims, 21 Drawing Sheets

(51) Int. Cl.
    *G06K 9/62*     (2022.01)
    *A61B 5/0215*     (2006.01)
    *A61B 5/00*     (2006.01)

(52) U.S. Cl.
    CPC ........ *A61B 5/02158* (2013.01); *A61B 5/1116* (2013.01); *A61B 5/1118* (2013.01); *G06K 9/6218* (2013.01); *G06K 9/6269* (2013.01)

(58) Field of Classification Search
    CPC ... A61B 5/1116; A61B 5/1118; A61B 5/1122; A61B 5/1123; A61B 5/341; A61B 5/686; A61B 5/7207; A61B 5/7221; A61B 5/7264; G06K 9/6218; G06K 9/6269; G06V 40/103
    See application file for complete search history.

(56) References Cited

U.S. PATENT DOCUMENTS

| | | |
|---|---|---|
| 8,150,531 B2 | 4/2012 | Skelton |
| 8,323,218 B2 | 12/2012 | Davis et al. |
| 8,366,641 B2 | 2/2013 | Wang et al. |
| 8,388,555 B2 | 3/2013 | Panken et al. |
| 8,708,934 B2 | 4/2014 | Skelton et al. |
| 8,818,748 B2 | 8/2014 | Hatlestad et al. |
| 2007/0115277 A1 | 5/2007 | Wang et al. |
| 2007/0118056 A1 | 5/2007 | Wang et al. |
| 2010/0010338 A1 | 1/2010 | van Dam et al. |
| 2010/0010380 A1 | 1/2010 | Panken et al. |
| 2010/0010391 A1 | 1/2010 | Skelton et al. |
| 2010/0010580 A1 | 1/2010 | Skelton et al. |
| 2010/0010583 A1 | 1/2010 | Panken et al. |
| 2010/0280578 A1 | 11/2010 | Skelton et al. |
| 2011/0201969 A1 | 8/2011 | Hatlestad et al. |
| 2012/0323501 A1 | 12/2012 | Sarrafzadeh et al. |
| 2013/0116602 A1 | 5/2013 | Van Den et al. |
| 2014/0019080 A1 | 1/2014 | Chan et al. |
| 2016/0089059 A1 | 3/2016 | Hu |
| 2017/0113051 A1 | 4/2017 | Sheldon et al. |
| 2018/0035956 A1 | 2/2018 | Gunderson et al. |
| 2018/0177436 A1 | 6/2018 | Chang et al. |
| 2018/0220935 A1 | 8/2018 | Tadano et al. |

FOREIGN PATENT DOCUMENTS

| | | |
|---|---|---|
| EP | 1954192 B1 | 12/2017 |
| WO | 2010005816 A2 | 1/2010 |
| WO | 2012014110 A2 | 2/2012 |
| WO | 2016134306 A1 | 8/2016 |
| WO | 2017180929 A1 | 10/2017 |

OTHER PUBLICATIONS

U.S. Appl. No. 16/109,023, naming inventors Lee et al., filed Aug. 22, 2018.

AUTOMATIC DETECTION OF BODY PLANES OF ROTATION

This application claims the benefit of U.S. Provisional Application No. 62/902,751 which was filed on Sep. 19, 2019. The entire content of Application No. 62/902,751 is incorporated herein by reference.

TECHNICAL FIELD

The disclosure relates to body posture and body part orientation monitoring in medical devices.

BACKGROUND

Medical devices designed to be worn by or implanted in a patient may automatically monitor a variety of physiologic variables in patients. In some examples, medical devices may monitor physiologic variables over time, such as blood pressure or cardiac rhythm to provide caregivers trend information that may be useful in understanding a patient's health condition in order to provide physicians with evidence as to disease progression or resolution. In other examples, medical devices may automatically adjust therapy based on the measured patient's physical parameters.

Medical devices that include accelerometers may monitor patient parameters such as body posture, device orientation, activity level, heart rate, heart motion, and sound, including heart sounds, snoring, patient speech, and sound in the patient's environment. Posture sensing may be useful to provide posture trends, such as trends in sleeping orientations, that may help patients, caregivers, and physicians to be aware of and track trends or sudden changes in activities of daily living such as sleep time, sleep quality, and degree of activity.

SUMMARY

In general, the disclosure describes techniques for automatically detecting an orientation of an implantable medical device (IMD) within a patient. When an IMD is implanted in a patient, a clinician may calibrate a reference orientation of the IMD with respect to a given body posture. Subsequently, as the patient changes body posture, the orientation of the device may change. The IMD may detect such changes in the orientation of the device and use such information to determine posture changes of the body of the patient for monitoring patient parameters or controlling delivery of therapy. However, over time, the IMD may shift or rotate within the patient. This may induce error in the posture detection operations performed by the IMD, because a reference point used by the IMD may only remain valid as long as the relative position of the IMD with respect to the patient remains stable. Accordingly, over time, accumulated shifting, rotation, or other movement of the IMD may require recalibration to account for the new position and/or orientation relative to the patient's body.

Techniques are described herein that allow an IMD to automatically recalibrate a reference orientation and perform posture detection, even as the position and/or orientation of the IMD changes within the body of the patient. For example, one or more sensors of an IMD sense a plurality of orientation vectors of the IMD with respect to a gravitational field. Processing circuitry of the IMD (or another computing device in communication with the IMD) processes the plurality of orientation vectors to identify an upright vector of the plurality of orientation vectors. For example, by assuming that a patient is in an upright position most of the time and/or during daytime hours, an average vector of the plurality of orientation vectors may be assumed to correspond to an upright posture of the patient. The processing circuitry classifies the plurality of orientation vectors with respect to the upright vector to define a sagittal plane of the patient and a transverse plane of the patient. The processing circuitry determines, based on the upright vector, the sagittal plane, and the transverse plane, an orientation of the IMD within the patient. Furthermore, the processing circuitry may use the orientation of the IMD within the patient to determine a current posture of the patient. Therefore, an IMD in accordance with the techniques of the disclosure may recalibrate its current orientation and accurately detect a posture of the patient, even as the position and/or orientation of the IMD within the patient changes over time. Such an IMD may reduce or obviate the need for a clinician to periodically and manually recalibrate an orientation of the IMD with respect to the patient.

In one example, this disclosure describes a method comprising: sensing, by one or more sensors of an implantable medical device (IMD), a plurality of orientation vectors of the IMD with respect to a gravitational field; processing, by processing circuitry of the IMD, the plurality of orientation vectors to identify an upright vector of the plurality of orientation vectors, the upright vector corresponding to an upright posture of a patient; classifying, by the processing circuitry, the plurality of orientation vectors with respect to the upright vector to define a transverse plane of the patient; classifying, by the processing circuitry, the plurality of orientation vectors with respect to the upright vector to define a sagittal plane of the patient; and determining, by the processing circuitry and based on the upright vector, the transverse plane, and the sagittal plane, a reference orientation of the IMD.

In another example, this disclosure describes an implantable medical device (IMD) comprising: one or more sensors configured to sense a plurality of orientation vectors of the IMD with respect to a gravitational field; and processing circuitry configured to: process the plurality of orientation vectors to identify an upright vector of the plurality of orientation vectors, the upright vector corresponding to an upright posture of a patient; classify the plurality of orientation vectors with respect to the upright vector to define a transverse plane of the patient; classify the plurality of orientation vectors with respect to the upright vector to define a sagittal plane of the patient; and determine, based on the upright vector, the transverse plane, and the sagittal plane, a reference orientation of the IMD.

In another example, this disclosure describes a non-transitory, computer-readable medium comprising instructions that, when executed, are configured to cause processing circuitry of an implantable medical device (IMD) to: receive, from one or more sensors, a plurality of orientation vectors of the IMD sensed with respect to a gravitational field; and process the plurality of orientation vectors to identify an upright vector of the plurality of orientation vectors, the upright vector corresponding to an upright posture of the patient; classify the plurality of orientation vectors with respect to the upright vector to define a transverse plane of the patient; classify the plurality of orientation vectors with respect to the upright vector to define a sagittal plane of the patient; and determine, based on the upright vector, the transverse plane, and the sagittal plane, a reference orientation of the IMD.

In another example, this disclosure describes a system comprising: one or more sensors configured to sense a plurality of orientation vectors of an implantable medical device (IMD) with respect to a gravitational field; and processing circuitry configured to: process the plurality of orientation vectors to identify an upright vector of the plurality of orientation vectors, the upright vector corresponding to an upright posture of a patient; classify the plurality of orientation vectors with respect to the upright vector to define a transverse plane of the patient; classify the plurality of orientation vectors with respect to the upright vector to define a sagittal plane of the patient; and determine, based on the upright vector, the transverse plane, and the sagittal plane, a reference orientation of the IMD.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
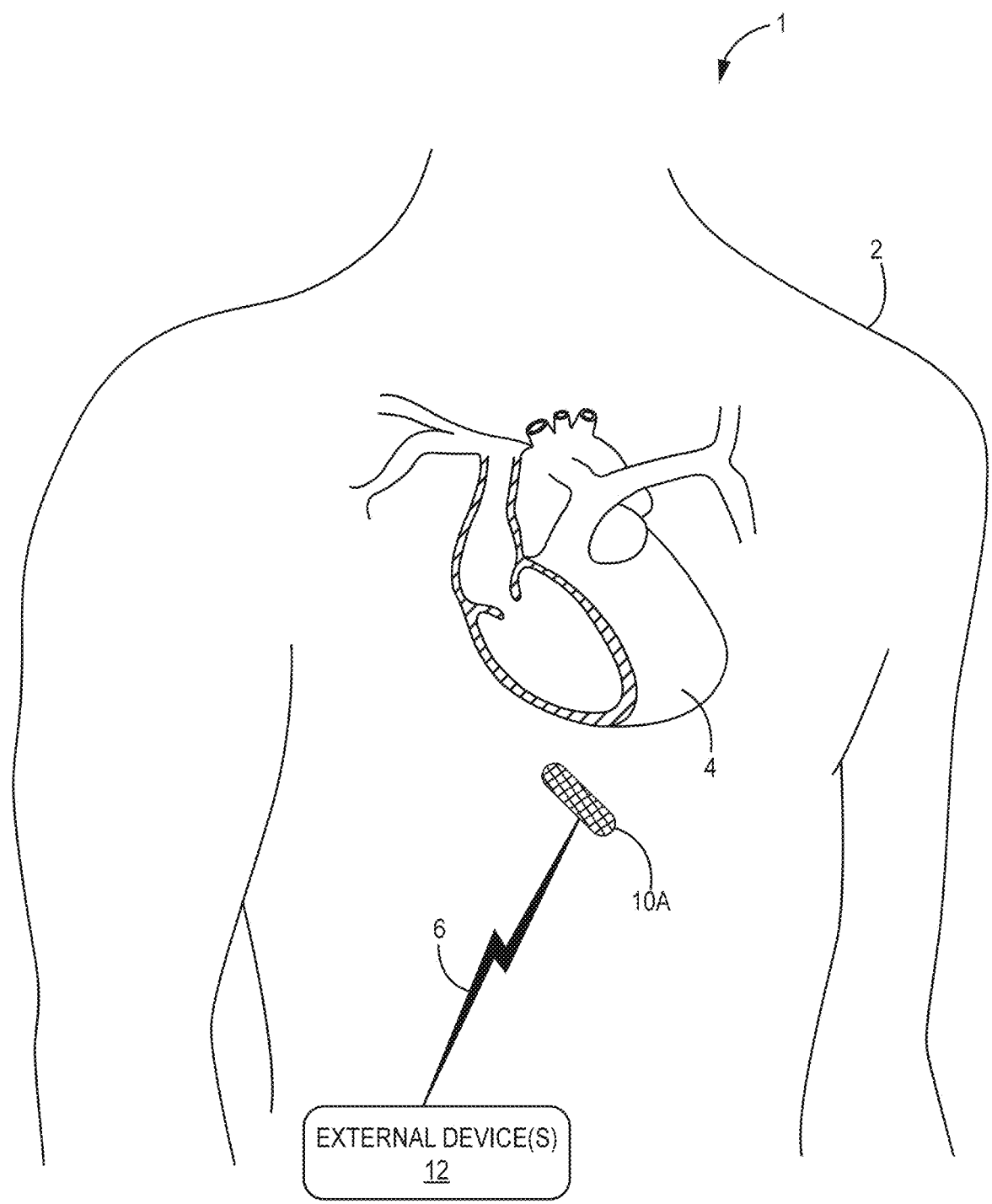
FIG. 1 is a conceptual diagram illustrating an example medical device system configured to automatically detect an orientation of a medical device according to one or more techniques of this disclosure.

FIG. 1 is a conceptual diagram illustrating example medical device system 1 configured to automatically detect an orientation of medical device 10 according to one or more techniques of this disclosure. Example medical system 1 also may be referred to as a "medical system" or a "system." In general, systems (e.g., system 1) may include one or more medical devices, leads, implanted or external sensors, external devices, or other components configured for techniques described herein. Medical system 1 is an example of a medical device system configured to implement the techniques described herein for monitoring the chest orientation, body posture, and other physiological parameters of patient 2, which may include blood pressure, patient motion, patient activity, or heart rate. In the illustrated example, medical system 1 includes an implantable medical device (IMD) 10 (also may be referred to as an implantable monitoring device, an implantable hub device, or an insertable cardiac monitor (ICM)), such as may be in communication with one or more external devices 12 or one or more other implanted devices, not shown in FIG. 1. Such other implantable devices may be an implantable pacemaker, an implantable cardiac defibrillator, a cardiac resynchronization therapy (CRT) device (e.g., CRT-D defibrillator or CRT-P pacemaker), a neuro-stimulator, a nerve stimulator, a drug pump (e.g., an insulin pump), or other devices. In some examples, some of these devices may alternatively be external medical devices, such as the insulin pump. In some examples another implantable device, also not shown, may include an implantable pressure sensing device that may be implanted within a pulmonary artery of heart 4. The communication link between external device 12 and IMD 10A is indicated by communication link 6.

In the example of FIG. 1, IMD 10A is an insertable cardiac monitor (ICM) capable of sensing and recording electrocardiogram (ECG) signals from a location outside of heart 4 via electrodes. In some examples, IMD 10A includes or is coupled to one or more additional sensors, such as accelerometers, that generate one or more signals that vary based on patient motion or chest orientation, blood flow, impedance, heart rate, oxygen saturation, or respiration. IMD 10A may monitor a physiological parameter indicative of patient state, such as posture, heart rate, activity level, heart rate, or respiration rate, and IMD 10A may measure the one or more physiological parameters at times when another implantable medical device, not shown, is measuring cardiovascular pressure. IMD 10A may include a light emitter and light detector configured to emit a signal (e.g., a light signal) into a target site of patient 2.

IMD 10A may include processing circuitry as well as a sensor, such as a 3-axis accelerometer, that is responsive to a gravitational field. The processing circuitry of IMD 10A may receive the outputs of the sensor and determine the posture of patient 2, based on the outputs of the sensor. The posture information of patient 2 sensed by IMD 10A may be used for monitoring of patent parameters or controlling delivery of therapy by IMD 10A. For example, day and night metrics, such as a sleep onset time and a sleep end time, a number of out-of-bed events at night, or an amount of time spent laying down during the day may be used by a clinician to guide delivery of therapy to patient 2. For example, determining that patient 2 has a history of sleeping in a variety of recumbent postures when sleeping but now only sleeps in a supine position may indicate a change in a medical condition of patient 2. Additionally, determining that an activity level of patient 2 has remained stable over a period of time, but patient 2 has spent more time laying down during the day may also indicate a change in a medical condition of patient 2. Furthermore, the use of posture may be used to activate or deactivate the collection of patient parameters by IMD 10A. For example, IMD 10A may only collect respiration data for patient 2 when patient 2 is standing upright. IMD 10A may sense a plurality of different postures of patient 2, including, for example, an upright or standing position, a prone position, a supine position, a left lateral recumbent (left-side laying) position, or a right lateral recumbent (right-side laying) position.

In some examples, IMD 10A may be implanted outside of the thoracic cavity of patient 2 (e.g., subcutaneously or submuscularly, such as the pectoral location). IMD 10A may be positioned near the sternum near or just below the level of heart 4. In some examples, IMD 10A may take the form of a Reveal LINQ™ ICM, available from Medtronic plc, of Dublin, Ireland. In other examples, IMD 10A may take the form of another physiological monitor or tracker, a pacemaker, defibrillator, drug delivery system or other types of medical device, or any other implantable or external device.

IMD 10A may include a timer and processing circuitry configured to determine a time of day based on the timer value or may determine the amount of time between events (e.g., posture changes). IMD 10A may include wireless communication circuitry configured to transmit or receive a signal from another device, such as to or from one or more external devices 12, or to another implanted medical device, for example. IMD 10A may determine a patient's posture, for example, and transmit that determination to external device 12.

IMD 10A may transmit data about the posture, and other physiological parameter data acquired by IMD 10A, to external device 12. For example, IMD 10A may transmit any data described herein related to cardiovascular pressure, posture, heart rate, activity level, respiration rate, or other physiological parameters to external device 12. For purposes of this disclosure, a chest posture, or other physiological measurements may include one or more numerical values, multi-variable tables (e.g., such values as a function of time), or other techniques for storing such data.

External device 12 may include processing circuitry configured to communicate, execute programming instructions, provide alerts to a patient or others and perform other functions. In some examples, external device 12 may be a computing device (e.g., used in a home, ambulatory, clinic, or hospital setting) to communicate with IMD 10A via wireless telemetry. External device 12 may include or be coupled to a remote patient monitoring system, such as Carelink®, available from Medtronic plc, of Dublin, Ireland. External device 12 may be, as an example, a programmer, external monitor, or a consumer device (e.g., a smart phone). In some examples, external device 12 may receive data, alerts, patient instructions, or other information from IMD 10A.

External device 12 may be used to program commands or operating parameters into IMD 10A for controlling its functioning (e.g., when configured as a programmer for IMD 10A). External device 12 may be used to interrogate IMD 10A to retrieve data, including device operational data as well as physiological data accumulated in IMD memory. The interrogation may be automatic, such as according to a schedule, or in response to a remote or local user command. Programmers, external monitors, and consumer devices are examples of external devices 12 that may be used to interrogate IMD 10A. Examples of communication techniques used by IMD 10A and external device 12 include radiofrequency (RF) telemetry, which may be an RF link established via Bluetooth, WiFi, or medical implant communication service (MICS). In other words, medical system 1 is an example of a medical device system configured to determine, monitor and track the chest orientation, posture, and activity of patient 2. The techniques described herein may be performed by processing circuitry of medical system 1, such as processing circuitry of one or more of IMD 10A, external device 12, and one or more other implanted or external devices not shown, individually, or collectively.

In accordance with the techniques of the disclosure, IMD 10A automatically detects and calibrates a reference orientation of IMD 10A within patient 2. As described herein, "calibrating" IMD 10A refers to determining a reference orientation of IMD 10A within patient 2 for subsequent use in determining a posture of patient 2. When IMD 10A is implanted in patient 2, a clinician may calibrate a reference orientation of IMD 10A with respect to a body of patient 2. Subsequently, as patient 2 changes posture, the orientation of a body part of patient 2 within which IMD 10A is implanted, and/or an orientation of IMD 10A, may change. IMD 10A may detect such changes in the orientation of IMD 10A with respect to patient 2 and use such information to determine posture changes of patient 2 for monitoring patient parameters or controlling delivery of therapy. However, over time, IMD 10A may shift or rotate within patient 2. This may induce error in the posture detection operations performed by IMD 10A, because a reference point used by IMD 10A to determine posture may only remain valid as long as the relative position of IMD 10A with respect to patient 2 remains stable. Accordingly, over time, accumulated shifting, rotation, or other movement of IMD 10A may require the recalibration to account for the new position and/or orientation of IMD 10A.

As described herein, IMD 10 performs automatic detection of body planes of rotation of patient 2. For example, IMD 10A automatically recalibrates a reference orientation to accurately perform posture detection of patient 2, even as the position and/or orientation of IMD 10A changes within the body of patient 2. In one example of the techniques of the disclosure, one or more sensors of IMD 10A sense a plurality of orientation vectors of IMD 10A with respect to a gravitational field. IMD 10A processes the plurality of orientation vectors to identify an upright vector of the plurality of orientation vectors. For example, by assuming that patient 2 is in an upright position most of the time, or during daytime hours, an average vector of the plurality of orientation vectors may be assumed to correspond to an upright posture of patient 2. IMD 10A classifies the plurality of orientation vectors with respect to the upright vector to define a sagittal plane of patient 2 and a transverse plane of patient 2. IMD 10A determines, based on the upright vector, the sagittal plane, and the transverse plane, a reference orientation of IMD 10A within patient 2. Furthermore, IMD 10A may use determined orientation of IMD 10A within patient 2 to determine a current posture of patient 2. Therefore, IMD 10A, operating in accordance with the techniques of the disclosure, may recalibrate a reference orientation of IMD 10A with respect to patient 2 and accurately detect a posture of patient 2, even as the position and/or orientation of IMD 10A within patient 2 changes over time. Therefore, by using the techniques of the disclosure, IMD 10A may reduce or obviate the need for a clinician a caregiver, or patient 2 to periodically and manually recalibrate the reference orientation of IMD 10A with respect to patient 2.

Figure 2:
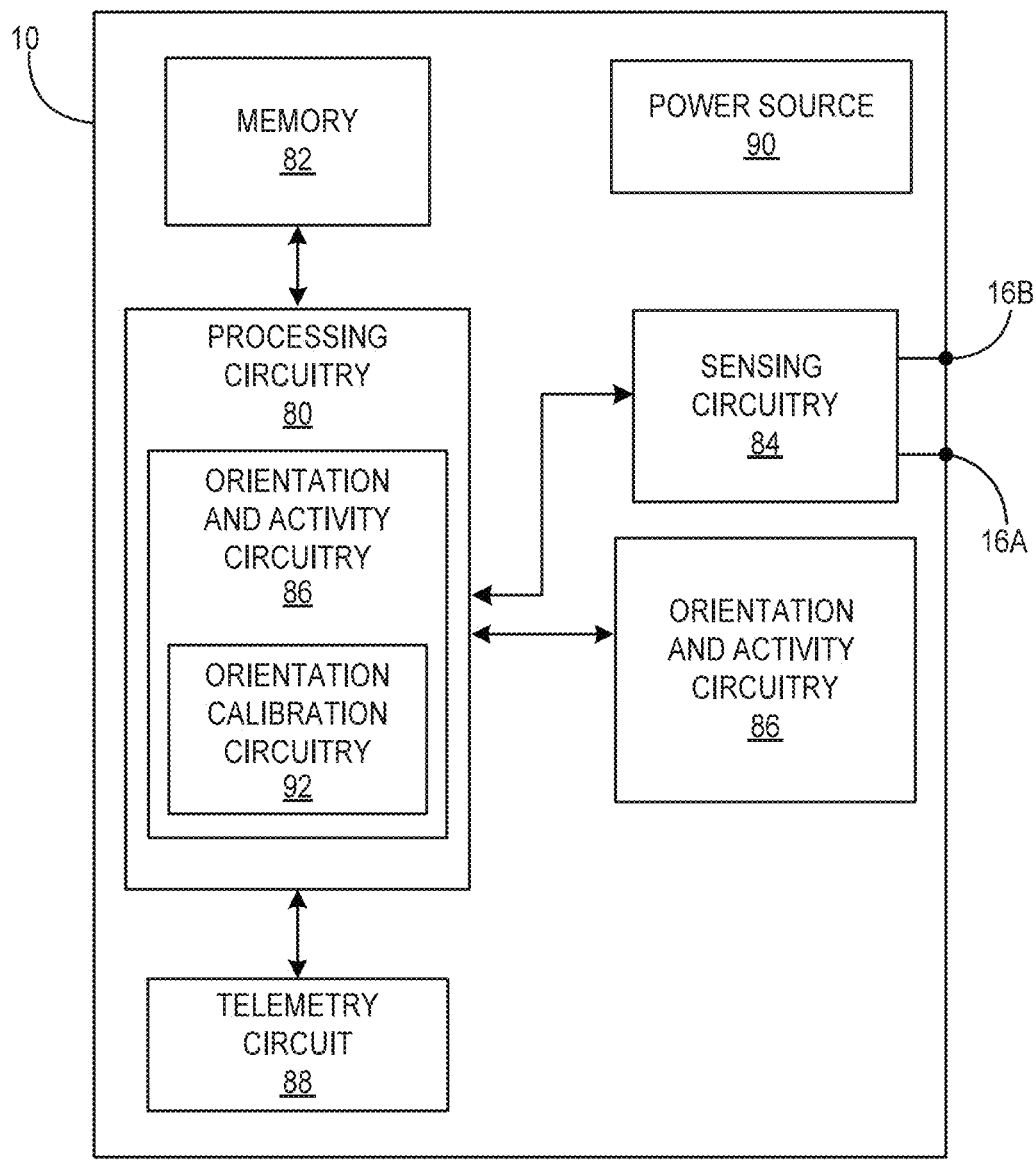
FIG. 2 is a functional block diagram of an example medical device configured to automatically detect an orientation of the medical device of FIG. 1 according to one or more techniques of this disclosure.

FIG. 2 is a functional block diagram illustrating various components of an IMD 10. IMD 10 of FIG. 2 may include the same functions and features as described above for IMD 10A in relation to FIG. 1. Similarly, the description of IMD 10 below may also apply to other medical devices with orientation and activity state sensing circuitry that may be attached to a patient, such as by straps or other means.

In the example of FIG. 2, IMD 10 includes a processing circuitry 80, memory 82, sensing circuitry 84, telemetry circuit 88, and power source 90. Processing circuitry 80 includes orientation and activity circuitry 86 and orientation calibration circuitry 92. Memory 82 may store instructions for execution by processing circuitry 80, stimulation therapy data, orientation and activity state information, orientation and activity state indications, and any other information regarding therapy or patient 2, as depicted in FIG. 1. Therapy information may be recorded for long-term storage and retrieval by a user, and the therapy information may include any data created by or stored in IMD 10.

Memory 82 may include separate memories for storing instructions, orientation and activity state information, program histories, and any other data that may benefit from separate physical memory modules. In some examples, memory 82 is random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, memory 82$y$ may be implanted entirely in hardware, software, or a combination thereof.

Processing circuitry 80 controls sensing circuitry 84 to sense physiological signals via electrode combinations formed by electrodes in one or more electrode arrays. For example, sensing circuitry 84 may receive signals, e.g., cardiac electrogram signals, via electrodes on one or more leads 16A and 16B. Components described as processors, or processing circuitry within IMD 10, external device 12, as described above in relation to FIG. 1, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Sensing circuitry 84 may be configured to switch between one or more sensing vectors via electrodes, such as in an electrode array. In some examples, sensing circuitry 84 may be configured to sense muscle activity, impedance changes and sensing electrical activity of the heart. Though not shown, some examples of medical devices that perform the orientation and activity sensing techniques of this disclosure may include medical devices that are configured to deliver therapy, such as drug therapy, or electrical stimulation therapy. Such medical devices may include therapy generation circuitry instead of or in addition to sensing circuitry, as well as chemical detection, light or temperature detection or other sensors. Some example medical devices may include a cardiac pacemaker, a cardioverter, a defibrillator and a neurostimulator.

In some examples, IMD 10 may additionally or alternatively be configured to sense one or more physiological parameters of patient 2. For example, physiological parameters may include heart rate, electromyography (EMG), an electroencephalogram (EEG), an electrocardiogram (ECG), temperature, respiration rate, or pH. These physiological parameters may be used by processing circuitry 80, in some examples, to confirm or reject changes in sensed orientation and activity state that may result from vibration, patient travel (e.g., in an aircraft, car or train), or some other false positive of orientation and activity state. In some examples, processing circuitry 80 may use heart rate, activity, and/or time of day (as examples) to assume or confirm a patient is upright (awake and active) or laying down (asleep and inactive).

Wireless telemetry in IMD 10 with external device 12, or another device may be accomplished, for example, by radio frequency (RF) communication, proximal inductive interaction, or tissue conductance communication (TCC) of IMD 10 with device 12. Telemetry circuit 88 may send information to and receive information from external device 12 on a continuous basis, at periodic intervals, at non-periodic intervals, or upon request from the stimulator or programmer. To support wireless communication, telemetry circuit 88 may include appropriate electronic components, such as amplifiers, filters, mixers, encoders, decoders, and the like.

Power source 90 delivers operating power to the components of IMD 10. Power source 90 may include a small rechargeable or non-rechargeable battery and a power generation circuit to produce the operating power. Recharging may be accomplished through proximal inductive interaction between an external charger and an inductive charging coil within IMD 10. As one example, external device 12 may include the charger to recharge power source 90 of IMD 10. Hence, the programmer and charger may be integrated in the same device. Alternatively, in some cases, a charger unit may serve as an intermediate device that communicates with both the IMD and the programmer. In some examples, power requirements may be small enough to allow IMD 10 to utilize patient motion and implement a kinetic energy-scavenging device to trickle charge a rechargeable battery. In other examples, traditional batteries may be used for a limited period of time. As a further alternative, an external inductive power supply could transcutaneously power IMD 10 when needed or desired.

Orientation and activity circuitry 86 allows IMD 10 to sense the body posture and activity state, e.g., body part orientation, activity, or any other static orientation or motion of patient 2. Orientation and activity circuitry 86 may include circuitry suitable for amplifying, filtering or otherwise processing signals received from orientation and activity sensor 87. Orientation and activity state information generated by orientation and activity circuitry 86 and processing circuitry 80 may correspond to an activity and/or posture undertaken by patient 2 or a gross level of physical activity, e.g., activity counts based on footfalls or the like.

In the example of FIG. 2, orientation and activity circuitry 86 may receive signals from orientation and activity sensor 87. Orientation and activity sensor 87 include one or more accelerometers, such as 3-axis accelerometers, capable of detecting static orientation or vectors in three-dimensions. In some examples the one or more accelerometers may be responsive to a gravitational field. For example, orientation and activity sensor 87 may include one or more micro-electro-mechanical accelerometers. In other examples, orientation and activity sensor(s) 87 may alternatively or additionally include one or more gyroscopes, pressure transducers or other sensors to sense the posture and activity of patient 2. Although orientation and activity sensor 87 is described as containing the 3-axis accelerometer, orientation and activity sensor 87 may contain multiple single-axis accelerometers, dual-axis accelerometers, 3-axis accelerometers, or some combination thereof.

In some examples, processing circuitry 80 processes an analog output of the orientation and activity sensor 87 in orientation and activity circuitry 86 to determine activity and/or orientation data. For example, orientation and activity circuitry 86 of processing circuitry 80 may process the raw signals provided by orientation and activity sensor 87 to determine activity counts. In some examples, processing circuitry 80 may process the signals provided by orientation and activity state sensor 87 to determine velocity of motion information along each axis. In this disclosure, the term "sensor" refers to an orientation and activity sensor 87, such as an accelerometer, unless otherwise noted.

In one example, each of the x, y, and z signals provided by the orientation and activity sensor 87 has both a DC component and an AC component. The DC components may describe the gravitational force exerted upon the sensor and may thereby be used to determine orientation of the sensor within the gravitational field of the earth. In other words, the sensor may be responsive to a gravitational field. Assuming the orientation of the sensor is relatively fixed with respect to patient 2, the DC components of the x, y and z signals may be utilized to determine the patient's body part orientation within the gravitational field, and hence to determine the body posture of the patient or the patient's body part orientation. In other words, processing circuitry 80 may receive the outputs of orientation and activity state sensor 87 and determine an orientation vector of orientation and activity state sensor 87 relative to a gravitational vector of the gravitational field. As a result of determining the orientation of orientation and activity state sensor 87 relative to the patient's body part orientation, processing circuitry 80 may determine the body part orientation or, in some examples, a body posture of the patient. The x, y and z signals may be interpreted by processing circuitry 80 as an orientation vector of the sensor [ax, ay, az].

The AC component of the x, y and z signals may yield information about patient motion. In particular, the AC component of a signal may be used to derive a value for an activity describing the patient's motion in one or more combinations of axes. This activity may involve a level, direction of motion, or acceleration of patient 2.

One method for determining the activity is an activity count. An activity count may be used to indicate the activity or activity level of patient 2. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count."

The number "N" of consecutive samples may be selected by orientation and activity circuitry 86 of processing circuitry 80 based on the current orientation and activity state, in some examples. The activity count may be the activity portion of the orientation and activity state parameter value that may be associated with the orientation portion. The resulting orientation and activity state parameter value may then incorporate both activity and orientation to generate an accurate indication of the motion of patient 2. In some examples, the posture portion of the orientation and activity state parameter may include the posture, e.g. upright, lying down, or a combination of back-angle and side-angle. In some examples, the orientation and activity state parameter may include the orientation vector of the sensor.

As another example, the activity portion of the orientation and activity state parameter value may describe a direction of motion. This activity parameter may be associated with one or more directional activity vectors describing activity levels in 3 dimensions. Another example of an activity parameter relates to acceleration in particular directions. A value quantifying the magnitude and orientation of the largest directional change of motion over a period of time may be associated with the activity portion of an orientation and activity state parameter value.

Processing circuitry 80 may store orientation and activity state information in memory 82 for later review by a clinician, used to adjust therapy, present an orientation and activity state indication to patient 2, or some combination thereof. As an example, processing circuitry 80 may record the orientation and activity state parameter value, or output, of the 3-axis accelerometer and assign the orientation and activity state parameter value to a certain predefined posture indicated by the orientation and activity state parameter value. In this manner, IMD 10 may be able to track how often and how long patient 2 remains within a certain posture.

In some examples, processing circuitry 80 may also adjust therapy or sensing (e.g., change an electrode vector, stimulation waveform parameter, or sensing threshold for one or more physiological parameters) for a new orientation when orientation and activity circuitry 86 indicates that patient 2 has in fact changed postures. Therefore, IMD 10 may be configured to provide posture responsive therapy or sensing to patient 2. Therapy or sensing adjustments in response to orientation and activity state may be automatic or semi-automatic (e.g., subject to patient approval). In many cases, fully automatic adjustments may be desirable so that IMD 10 may react more quickly to orientation and activity state changes.

An orientation and activity state parameter value from orientation and activity circuitry 86 that indicates the orientation and activity state may constantly vary throughout the day of patient 2. However, a certain activity (e.g., walking, running, or biking) or a posture (e.g., standing, sitting, or lying down) may include multiple orientation and activity state parameter values from orientation and activity circuitry 86. Memory 82 may include definitions for each orientation and activity state of patient 2.

Posture responsive stimulation may allow IMD 10 to implement a certain level of automation in therapy adjustments. Automatically adjusting stimulation may free patient 2 from the constant task of manually adjusting therapy each time patient 2 changes posture or starts and stops a certain orientation and activity state. Such manual adjustment of stimulation parameters can be tedious, requiring patient 2 to, for example, depress one or more keys of external device 12 multiple times during changes in patient posture or activity state to maintain adequate symptom control. In some examples, patient 2 may eventually be able to receive orientation and activity state responsive stimulation therapy without the need to continue making changes for different postures via external device 12. Instead, patient 2 may transition immediately or over time to fully automatic adjustments based on their orientation and activity state.

As described above, orientation and activity sensor 87 include one or more accelerometers, such as 3-axis accelerometers, capable of detecting static orientation or vectors in three-dimensions. In some examples the one or more accelerometers may be responsive to a gravitational field. When IMD 10A is implanted in patient 2, a clinician may calibrate orientation and activity sensor 87 with respect to a known orientation of IMD 10A and a body posture of patient 2. For example, the clinician may record a value of an accelerometer of orientation and activity sensor 87 along an X, Y, and Z direction for each of a plurality of postures of patient 2 and store the accelerometer values as reference values. Subsequently, orientation and calibration circuitry 80 may compare values of the accelerometer of orientation and activity sensor 87 to the reference values to determine a posture that patient 2 is assuming. Processing circuitry 80 use the detected changes in posture to inform the monitoring of patient parameters or for controlling delivery of therapy to patient 2.

However, over time, IMD 10 may shift or rotate within patient 2. This may induce error in the posture detection operations performed by IMD 10. For example, if IMD 10 changes position within patient 2, the reference values of orientation and activity sensor 87 may no longer correspond to the actual posture that patient 2 is assuming.

In accordance with the techniques of the disclosure, orientation and activity circuitry 86 further includes orientation calibration circuitry 92. Orientation calibration circuitry 92 may automatically and periodically recalibrate a reference orientation of IMD 10 with respect to the body of patient 2. Therefore, orientation calibration circuitry 92 may ensure that orientation and activity circuitry 86 may accurately detect a posture of patient 2, even as the position and/or orientation of IMD 10 changes within the body of patient 2. Therefore, by using the techniques of the disclosure, orientation calibration circuitry 92 may reduce or obviate the need for a clinician to periodically and manually recalibrate a reference orientation of IMD 10 with respect to patient 2. Without the use of the techniques of the disclosure, a clinician may be required to periodically recalibrate the reference orientation of IMD 10. Furthermore, if IMD 10 is not recalibrated frequently, patient parametric data obtained by IMD 10 may be inaccurate or unusable.

In one example of the techniques of the disclosure, one or more sensors of IMD 10A sense a plurality of orientation vectors of IMD 10A with respect to a gravitational field. IMD 10A processes the plurality of orientation vectors to identify an upright vector of the plurality of orientation vectors. For example, by assuming that patient 2 is in an upright position most of the time, or during daytime hours, an average vector of the plurality of orientation vectors may be assumed to correspond to an upright posture of patient 2. IMD 10A classifies the plurality of orientation vectors with respect to the upright vector to define a sagittal plane of patient 2 and a transverse plane of patient 2. IMD 10A determines, based on the upright vector, the sagittal plane, and the transverse plane, a reference orientation of IMD 10A within patient 2. Furthermore, IMD 10A may use the determined reference orientation of IMD 10A within patient 2 to determine a current posture of patient 2. Therefore, IMD 10A, operating in accordance with the techniques of the disclosure, may recalibrate a reference orientation and accurately detect a posture of patient 2, even as the position and/or orientation of IMD 10A within patient 2 changes over time. Therefore, by using the techniques of the disclosure, IMD 10A may reduce or obviate the need for a clinician to periodically and manually recalibrate a reference orientation of IMD 10A with respect to patient 2.

In one example, orientation and activity sensor 87 senses a plurality of orientation vectors of IMD 10 with respect to a gravitational field. Typically, each orientation vector points opposite to the direction of Earth's gravitational field. Thus, the orientation vector may be assumed to point "upward," and may be used as a point of reference to determine a current orientation of IMD 10 with respect to Earth's gravitational field. The techniques of the disclosure further take advantage of various algorithms and assumed patient behavior to cluster a plurality of orientation vectors together such that orientation calibration circuitry 92 may estimate a reference orientation of IMD 10 with respect to a body of patient 2. By calibrating a position of IMD 10 with respect to Earth's gravitational field and estimating a reference orientation of IMD 10 with respect to the body of patient 2, orientation calibration circuitry 92 may estimate the posture of patient 2 without the use of an external reference point. Therefore, the orientation calibration circuitry 92 may recalibrate a reference orientation of IMD 10 with respect to the body of patient 2 and orientation and activity circuitry 86 may perform accurate posture detection of patient 2, even after IMD 10 shifts position within the body of patient 2.

Orientation calibration circuitry 92 processes the plurality of orientation vectors sensed by orientation and activity sensor 87 to identify an upright vector of the plurality of orientation vectors. The upright vector may correspond to an upright posture of patient 2, such as a standing or sitting posture. The techniques of the disclosure assume that a patient is in an upright position most of the time in a 24-hour period (or most of the time during daytime hours). Therefore, an average vector of the plurality of orientation vectors may be assumed to roughly correspond to an upright posture of the patient. However, the upright vector may be made more accurate by filtering a plurality of orientation vectors to obtain a set of vectors that are associated with a time of day patient 2 is expected to be active, or a high activity level of patient 2.

As one example for determining the upright vector, orientation and activity sensor 87 senses a plurality of orientation vectors of IMD 10 with respect to a gravitational field over a period of time. Orientation calibration circuitry 92 determines one or more orientation vectors of the plurality of orientation vectors that correspond to an activity level of patient 2 that exceeds a patient activity threshold. Orientation calibration circuitry 92 may average the one or more orientation vectors that correspond to an activity level of patient 2 that exceeds a patient activity threshold such that the average vector corresponds to the upright vector.

As another example for determining the upright vector, orientation and activity sensor 87 senses a plurality of orientation vectors of IMD 10 with respect to a gravitational field over a period of time. Orientation calibration circuitry 92 determines one or more orientation vectors of the plurality of orientation vectors that correspond to a walking activity of the patient. For example, orientation calibration circuitry 92 may detect steps within the signals generated by orientation and activity sensor 87, to determine when patient 2 is walking. For example, orientation and activity sensor 87 may include one or more accelerometers or pressure sensors that sense an impulse that occurs when patient 2 moves (e.g., takes a step, stands, walks). Orientation calibration circuitry 92 may process the impulses to determine whether or not patient 2 has taken an action, and classifies the action as a "step." Orientation calibration circuitry 92 may further count a number and frequency of the actions classified as "steps" to determine whether patient 2 is undergoing a walking activity. Orientation calibration circuitry 92 may select only those orientation vectors sensed concurrently with the walking activity of the patient. In some examples, orientation calibration circuitry 92 may average the one or more orientation vectors that correspond to an activity level of patient 2 that exceeds a patient activity threshold such that the average vector corresponds to the upright vector.

As another example for determining the upright vector, an external device, such as external device 12 of FIG. 1, may determine a posture of patient 2 and transmit the determined posture to IMD 10. For example, external device 12 may receive an input from a patient indicative of a posture that patient 2 has assumed. Additionally, external device 12 may comprise a pedometer, accelerometer, or other type of sensor capable of detecting a posture of patient 12. Orientation and activity sensor 87 senses a plurality of orientation vectors of IMD 10 with respect to a gravitational field over a period of time. Processing circuitry 80 receives, via telemetry circuit 88 and from external device 12, the determined posture of patient 2 for the sensed orientation vectors. Orientation calibration circuitry 92 determines, based on the sensed orientation vectors associated with the various postures of patient 2, one or more orientation vectors of the plurality of orientation vectors that correspond to an upright posture of the patient. Orientation calibration circuitry 92 may average the one or more orientation vectors that correspond to an activity level of patient 2 that exceeds a patient activity threshold such that the average vector corresponds to the upright vector.

Orientation calibration circuitry 92 classifies the plurality of orientation vectors with respect to the upright vector to define a transverse plane of patient 2. The transverse plane of patient 2 is a conceptual plane that roughly divides the body of patient 2 into an upper portion and a lower portion. The techniques of the disclosure assume that sensed orientation vectors sensed above and below the transverse plane of patient 2 may correspond to an upright position or a recumbent position of patient 2, respectively.

To determine the transverse plane, orientation calibration circuitry 92 determines, for each sensed orientation vector, an angle between the orientation vector and the upright vector. Orientation calibration circuitry 92 compares the angle between the orientation vector and the upright vector to a predetermined upright angle. For example, the predetermined upright angle is about 20 degrees from the upright angle. If the angle between the orientation vector and the upright vector is less than the predetermined upright angle, orientation calibration circuitry 92 classifies the respective orientation vector as one of a first subset of the plurality of orientation vectors associated with an upright posture of the patient. If the angle between the orientation vector and the upright vector is greater than or equal to the predetermined upright angle, orientation calibration circuitry 92 classifies the respective orientation vector as one of a second subset of the plurality of orientation vectors associated with a recumbent posture of the patient. Orientation calibration circuitry 92 defines the transverse plane of the patient as a plane between the first subset of the plurality of orientation vectors associated with the upright posture of the patient and the second subset of the plurality of orientation vectors associated with the recumbent posture of the patient.

Further, orientation calibration circuitry 92 classifies the plurality of orientation vectors with respect to the upright vector to define a sagittal plane of patient 2. The sagittal plane of patient 2 is an conceptual plane that roughly divides the body of patient 2 into a left half and a right half. The techniques of the disclosure assume that sensed orientation vectors sensed to the left and right of the sagittal plane of patient 2 may correspond to the patient laying on a left side or on a right side of the body (e.g., a left lateral recumbent or right lateral recumbent posture).

As one example for determining the sagittal plane, orientation calibration circuitry 92 associates each orientation vector with a grid element of a sphere based on an orientation of the orientation vector with respect to the upright vector. Orientation calibration circuitry 92 identifies a subset of the plurality of grid elements that form an angle with the upright vector that is less than a predetermined upright angle. In some examples, the predetermined upright angle is 20 degrees. Orientation calibration circuitry 92 applies a clustering algorithm to identify a cluster of grid elements of the plurality of grid elements that are neighbors to the subset of the plurality of grid elements. In some examples, a grid element is a neighbor of the subset of the plurality of grid elements if the grid element is offset from a grid element of the subset of the plurality of grid elements by less than 10 degrees. Orientation calibration circuitry 92 determines a main eigenvector for the cluster of grid elements. The main eigenvector comprises a higher eigenvalue than each other eigenvector of a plurality of eigenvectors of the cluster of grid elements. Orientation calibration circuitry 92 determines, based on the cross product of the upright vector with the main eigenvector, a normal vector which defines the sagittal plane of patient 2 in that the normal vector is perpendicular to the sagittal plane.

As another example for determining the sagittal plane, orientation calibration circuitry 92 classifies each orientation vector as one of a first subset of the plurality of orientation vectors associated with an upright posture of the patient or one of a second subset of the plurality of orientation vectors associated with an recumbent posture of the patient. Orientation calibration circuitry 92 calculates a plurality of cross products between each orientation vector of the first subset of the plurality of orientation vectors associated with the upright posture of the patient and each orientation vector of the second subset of the plurality of orientation vectors associated with the recumbent posture of the patient. Orientation calibration circuitry 92 determines a weighted mean of each of the cross products to obtain a normal vector which defines the sagittal plane of patient 2.

Orientation calibration circuitry 92 determines, based on the upright vector, the sagittal plane, and the transverse plane, a reference orientation of IMD 10 within patient 2. After orientation calibration circuitry 92 determines the reference orientation of IMD 10, orientation and activity circuitry 86 may use reference orientation to determine, based on a current orientation of IMD 10, a posture of patient 2. For example, orientation and activity sensor 87 senses an orientation vector of patient 2. Orientation and activity circuitry 86 compares the orientation vector to the upright vector, the transverse plane and the sagittal plane to determine a posture of patient 2. Generally speaking, if the orientation vector is similar to the upright vector and above the transverse plane, orientation and activity circuitry 86 determines that patient 2 is in an upright posture. If the orientation vector is not similar to the upright vector, below the transverse plane, and located approximately along the sagittal plane, orientation and activity circuitry 86 determines that patient 2 is in a prone or supine position. If the orientation vector is not similar to the upright vector, located approximately along the transverse plane, and to the left or right of the sagittal plane, orientation and activity circuitry 86 determines that patient 2 is in left lateral recumbent or right lateral recumbent position. Additional details in evaluating the orientation vector with respect to the upright vector, the transverse plane and the sagittal plane are described in greater detail below.

Because of some inherent sensor inaccuracies and modeling errors, the transverse plane, as constructed by orientation calibration circuitry 92, may or may not be coplanar with an actual, real-world sagittal plane of patient 2. Further, the sagittal plane, as constructed by orientation calibration circuitry 92, may or may not be coplanar with an actual, real-world transverse plane of patient 2. Furthermore, the transverse and sagittal planes constructed by orientation calibration circuitry 92 may not necessarily be perpendicular to one another (as the actual, real-world transverse and sagittal planes of patient 2 would be). However, an advantage of the techniques of the disclosure is that orientation calibration circuitry 92 may still accurately calibrate an orientation of IMD 10 with respect to the body of patient 2 such that orientation and activity circuitry 86 may accurately detect a posture of patient 2, even though the transverse and sagittal planes of patient 2 computed by orientation calibration circuitry 92 are not perpendicular to one another or coplanar with the actual, real-world transverse and sagittal planes of patient 2.

Figure 3:
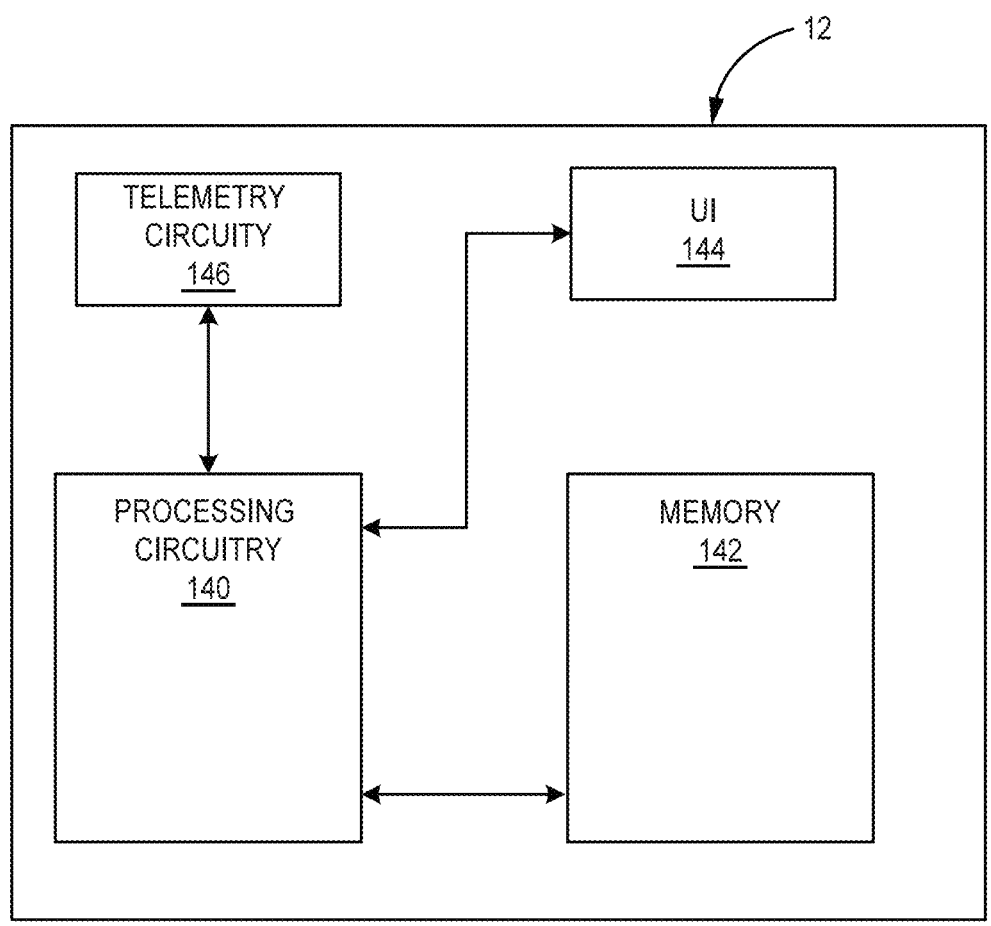
FIG. 3 is a functional block diagram of an example external computing device configured to communicate with a medical device.

FIG. 3 is a functional block diagram illustrating various components of an external device 12 for IMD 10, as depicted in FIG. 2. As shown in FIG. 3, external device 12 includes processing circuitry 140, memory 142, telemetry circuitry 146, user interface 144, and post-processing circuitry 112. A clinician or patient 2 may interact with user interface 144 to review information received by programmer 12 from IMD 10, such as orientation and activity states over time or other information described herein as being sensed and/or determined by IMD 10, and to program the sensing and/or stimulation functions of IMD 10, e.g., select values for parameters that control such functions.

Memory 142 includes operation instructions for processing circuitry 140 and data related to patient 2 and/or IMD 10, e.g., received from IMD 10. Memory 142 may also include operation instructions for other features of external device 12. In some examples, memory 142 is random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, memory 142 may be implanted entirely in hardware, software, or a combination thereof.

Telemetry circuitry 146 allows the transfer of data to and from IMD 10. Telemetry circuitry 146 may communicate automatically with IMD 10 at a scheduled time or when the telemetry circuit detects the proximity of the stimulator. Alternatively, telemetry circuitry 146 may communicate with IMD 10 when signaled by a user through user interface 144. To support wireless communication, telemetry circuitry 146 may include appropriate electronic components, such as amplifiers, filters, mixers, encoders, decoders, and the like. In some cases, external device 12 may be used when coupled to an alternating current (AC) outlet, e.g., AC line power, either directly or via an AC/DC adapter.

Figure 4:
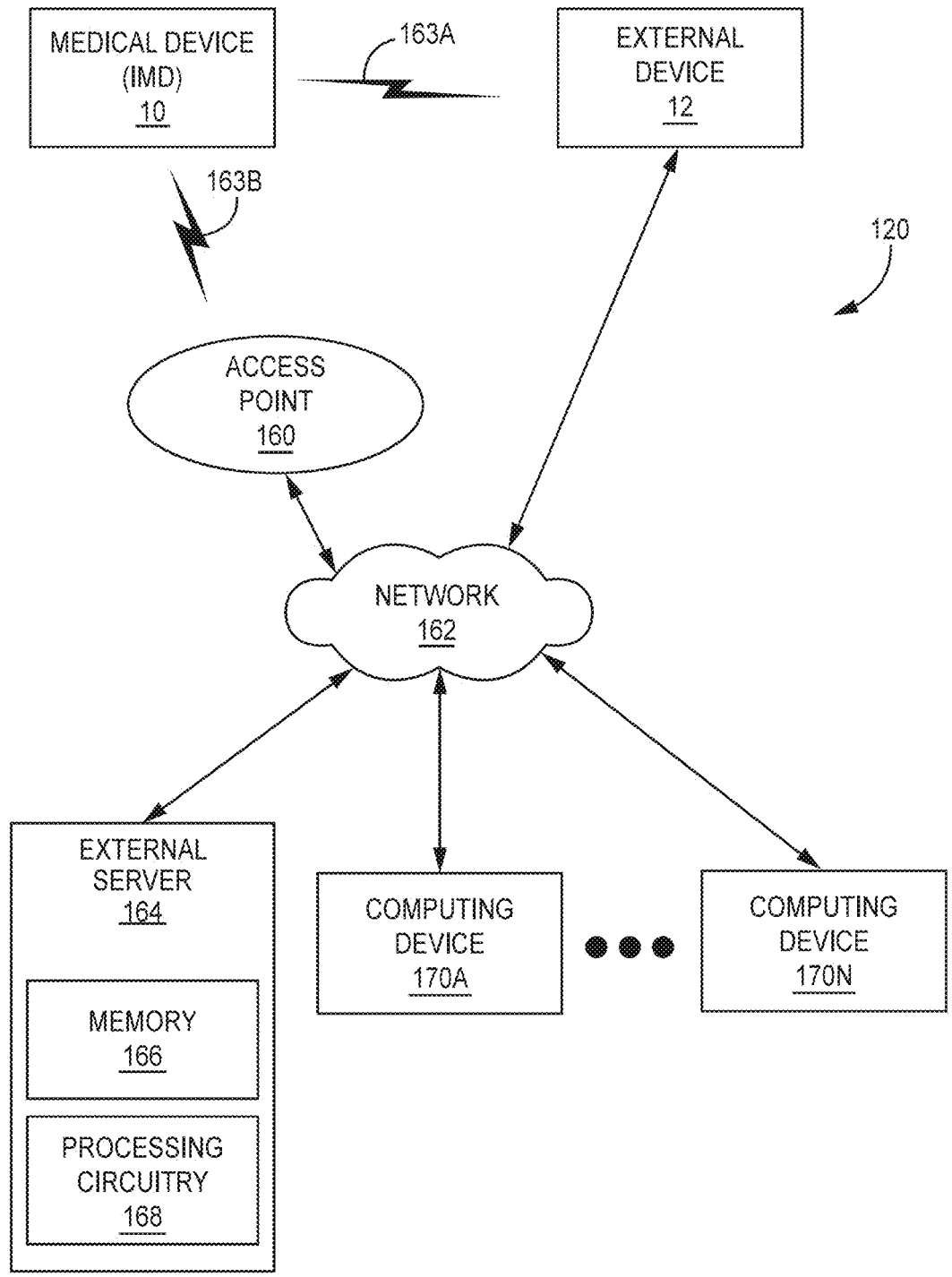
FIG. 4 is a functional block diagram illustrating an example system that includes external computing devices, such as a server and one or more other computing devices, that are coupled to the medical and the external computing device shown in FIG. 1 via a network.

FIG. 4 is a block diagram illustrating an example system 120 that includes an external device, such as a server 164, and one or more computing devices 170A-170N, that are coupled to IMD 10 and external device 12 shown in FIGS. 1 and 2, via a network 162. In this example, IMD 10 may use its telemetry circuit 88 to communicate with external device 12 via a first wireless connection 163A, and to communication with an access point 160 via a second wireless connection 163B.

In the example of FIG. 4, access point 160, external device 12, server 164, and computing devices 170A-170N are interconnected, and able to communicate with each other, through network 162. In some cases, one or more of access point 160, external device 12, server 164, and computing devices 170A-170N may be coupled to network 162 through one or more wireless connections. IMD 10, external device 12, server 164, and computing devices 170A-170N may each comprise one or more processors, such as processing circuitry 168. The one or more processors may include one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 160 may comprise a device, such as a home monitoring device, that connects to network 162 via any of a variety of connections, such as telephone dial-up, digital subscriber line (DSL), or cable modem connections. In other examples, access point 160 may be coupled to network 162 through different forms of connections, including wired or wireless connections.

During operation, IMD 10 may collect and store various forms of data. For example, IMD 10 may collect sensed orientation and activity state information that indicates how patient 2, as depicted in FIG. 1, moves throughout each day. In some cases, IMD 10 may directly analyze the collected data to evaluate the posture and activity state of patient 2, such as what percentage of time patient 2 was in each identified posture. In other cases, however, IMD 10 may send stored data relating to posture and activity state information to external device 12 and/or server 164 (e.g., processing circuitry 168 of server 164), either wirelessly or via access point 160 and network 162, for remote processing and analysis. For example, IMD 10 may sense, process, trend and evaluate the sensed posture and activity state information. Alternatively, processing, trending and evaluation functions may be distributed to other devices such as external device 12 or server 164 (e.g., processing circuitry 168 of server 164), which are coupled to network 162. In addition, posture and activity state information may be archived by any of such devices, e.g., for later retrieval and analysis by a clinician. For example, server 164 may archive posture and activity state information, which may include patient body angle, at memory 166.

In some cases, external device 12 or server 164 may process posture and activity state information, raw orientation data, other physiological sensing information, and/or therapy information into a displayable orientation and activity state report, which may be displayed via external device 12 or one of computing devices 170A-170N. The posture and activity state report may contain trend data for evaluation by a clinician, e.g., by visual inspection of graphic data. In some cases, the posture and activity state report may include the number of activities patient 2 conducted, a percentage of time patient 2 was in each posture and activity state, the average time patient 2 was continuously within an posture and activity state, and information regarding sensing and therapy delivery during each activity, or any other information relevant to patient 2 therapy, based on analysis and evaluation performed automatically by IMD 10, external device 12 or server 164. A clinician or other trained professional may review and/or annotate the posture and activity state report, and possibly identify any problems or issues with the physiological sensing or therapy that should be addressed.

In some cases, server 164 may be configured to provide a secure storage site for archival of posture and activity state information that has been collected from IMD 10 and/or external device 12. Network 162 may comprise a local area network, wide area network, or global network, such as the Internet. In some cases, external device 12 or server 164 may assemble posture and activity state information in web pages or other documents for viewing by trained professionals, such as clinicians, via viewing terminals associated with computing devices 170A-170N. System 120 may be implemented, in some aspects, with general network technology and functionality similar to that provided by the Medtronic CareLink® Network developed by Medtronic, Inc., of Minneapolis, Minn.

Although some examples of the disclosure may involve posture and activity state information and data, system 120 may be employed to distribute any information relating to the treatment of patient 2 and the operation of any device associated therewith. For example, system 120 may allow therapy errors or device errors to be immediately reported to the clinician. In addition, system 120 may allow the clinician to remotely intervene and reprogram IMD 10, external device 12, or communicate with patient 2. In an additional example, the clinician may utilize system 120 to monitor multiple patients and share data with other clinicians in an effort to coordinate rapid evolution of effective treatment of patients.

Furthermore, techniques of this disclosure may be applicable to IMDs that convey other therapies in which posture and activity state information is important, such as, e.g., deep brain stimulation (DBS), pelvic floor stimulation, gastric stimulation, occipital stimulation, functional electrical stimulation, cardiac pacing, anti-tachycardia therapies, and the like. Also, in some aspects, techniques for evaluating posture and activity state information, as described in this disclosure, may be applied to IMDs that are generally dedicated to sensing or monitoring and do not include stimulation or other therapy components, such as IMD 10.

Figure 5A:
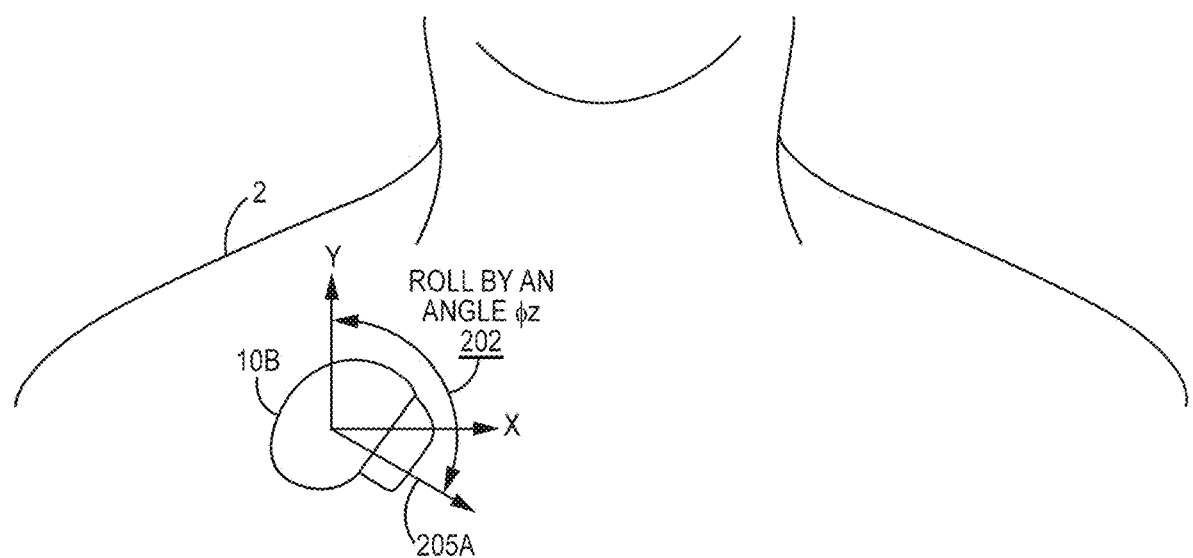
FIGS. 5A-5C are conceptual diagrams illustrating the roll, pitch and yaw angles of an example medical device which may be worn by or implanted in a patient.
Figure 5B:
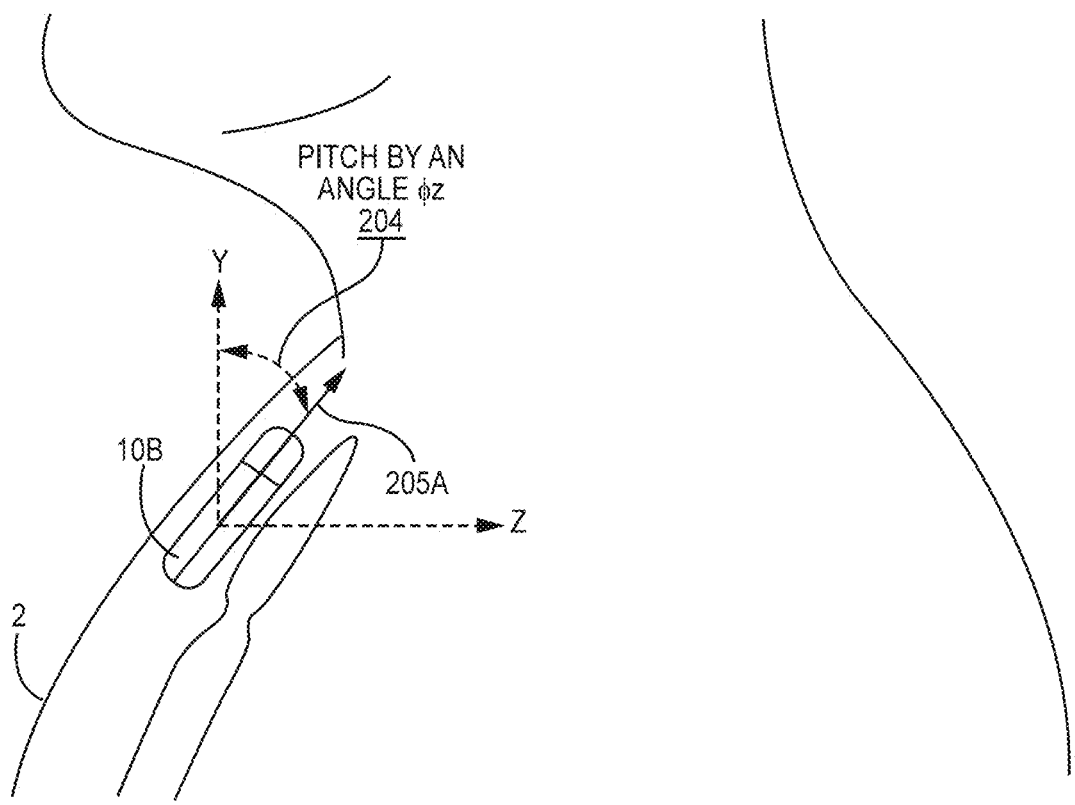
Figure 5C:
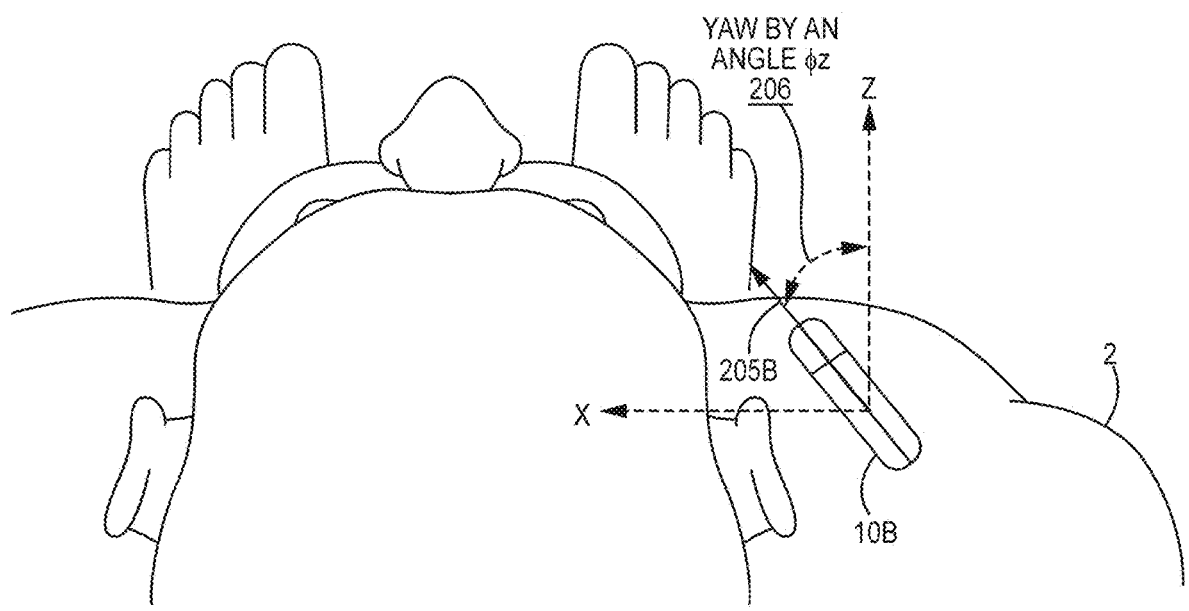

FIGS. 5A-5C are conceptual diagrams illustrating the roll, pitch and yaw angles of an IMD 10B. The techniques illustrated by FIGS. 5A-5C may also apply to any medical device which may be worn by or otherwise attached to a patient, e.g., with an arrangement of straps, or implanted in a patient.

3-Axis accelerometers have been used externally for short periods of time and placed on or about the body surface to monitor body posture, activity level and/or orientation and/or movement of specific limbs, or sections of the body for various purposes such as to aid in the diagnosis of various movement disorders, or automatically detecting falls. 3-axis accelerometers may also be used in implanted devices to do the same types of monitoring, but for a much longer period of time, e.g. months to years. Medical devices that include such 3-axis accelerometers may be useful to measure activity and body position and orientation parameters that can help recognize when patients are getting sicker, such as those suffering from heart failure, also called congestive heart failure (CHF). Such parameters may be combined and complemented with other physiologic metrics that also relate to the health condition of a patient, such as activity, impedance, body temperature, blood pressure, and heart rate.

To correctly monitor body posture or body part orientation, the axes of the accelerometers should be correctly aligned with the body or body part, or implement compensation means to correct for misalignment. In most external applications, the 3-axis accelerometers can be aligned in a consistent manner from subject to subject, by using holsters on a belt, or chest straps or tape. Device orientation compensation, however, may still be necessary to account for differences in body shapes or differences in the orientation of body parts from patient to patient. The degree of compensation depending on the required accuracy of the orientation measurements. The longer timeframe of implanted devices means implanted devices may be subject to changes in their orientation with time, for example from a patient's twiddling with the devices, soft tissue effects or other device migration. The device orientation compensation settings, as described in this disclosure, may be automatically updated periodically to account for these changes.

When utilizing a 3-axis accelerometer or other orientation sensor in an implanted device, not only do differences in body shape and orientation of body parts cause variability of the implant orientation of the internal 3-axis accelerometer relative to the earth's a gravitational field, but the orientation of the implant of the device may be chosen to, for example, for best use of the main diagnostic or therapeutic function of the device. For example, a medical device may be implanted in a position and orientation chosen to best receive ECG signals. Other factors in implanted device orientation and position may include to position the scar of the implant to minimize the visibility of the scar and optimize the performance of other sensors onboard the device, e.g. pH monitor, for example.

FIG. 5A illustrates an example roll angle 202 of the rotation of IMD 10B, with orientation vector 205A of a sensor, such as a 3-axis accelerometer. IMD 10B may include features similar to IMD 10A and IMD 10 as described above in relation to FIGS. 1 and 2. In the example of FIG. 5A, roll 202 is the angle around the ideal front-to-back central axis of the device and the angle of rotation is measured relative to the long axis of the patient. The long axis is a line running through the spine from the crown of the patient's head through the heels and is parallel to the Y-axis depicted in FIG. 5A. In other words, the orientation vector 205A is rotated at the roll angle 202 relative to the long axis of patient 2. IMD 10B may be substantially similar to IMD 10, or may be a different IMD, e.g., a cardiac pacemaker, cardioverter, and or defibrillator. IMD 10B may include circuitry, such processing circuitry 80, memory 82, orientation and activity sensor 87, and orientation and activity circuitry 86, described above with respect to IMD 10 in FIG. 2. Similar medical devices, including implantable or external devices, may implement the techniques described herein with respect to any of IMDs 10, 10A and 10B. The implantation locations of IMD 10B illustrated herein are merely examples, and medical devices implanted anywhere within patient or attached to the patient, e.g. with a harness or straps, may implement any of the techniques described herein.

FIG. 5B illustrates an example pitch angle 204 of IMD 10B as implanted in the patient. In the example of FIG. 5B, pitch 204 is the rotation angle about the left-right axis of the patient/device and is measured from a line parallel to the spine of patient 2. Orientation vector 205A is rotated about the left-right axis at the pitch angle 204.

For some applications, it may be necessary to account for the yaw of the implant. FIG. 5C illustrates an example a yaw 206 of device 200. In FIG. 5C, yaw is the rotation angle about the long axis of the patient, which is the Y-axis pointing straight out of FIG. 5C. Roll 202 is rotation measured from the long axis as compared to yaw 206, which is rotation about the long axis. Orientation vector 205A is used in FIG. 5C for clarity and is pointing 180 degrees from orientation vector 205A as shown in FIGS. 5A and 5B. Determining and compensating for yaw 206 may be valuable when it is important to recognize what position the patient is in when they are lying down. Laying down positions include supine (face up) and prone (face down), along with other positions such as right shoulder up, and so on.

A medical device processor, such as processing circuitry 80 depicted in FIG. 2, may determine orientation information by receiving outputs of a sensor that is responsive to a gravitational field, such as a 3-axis accelerometer. Based on the outputs of the sensor, a processor may determine an orientation vector of the sensor relative to a gravitational vector of the gravitational field. Also, by determining the orientation of the sensor in the medical device relative to the patient, e.g. determining the roll, pitch and yaw of the sensor relative to the patient, the processor may determine posture information of patient 2. In this disclosure, the process of determining the orientation of the sensor relative to the patient is called device orientation compensation, or simply compensation. In some examples the patient may be placed in a predetermined compensation posture, e.g. upright. Additional description of how processing circuitry 80 of IMD 10B may determine orientation information by receiving outputs of a sensor that is responsive to a gravitational field is described in more detail in Lee et al., U.S. patent application Ser. No. 16/109,023, entitled "BODY AND BODY PART ORIENTATION AND POSTURE MONITORING" and filed on Aug. 22, 2018, the entire content of which is incorporated by reference herein.

The examples shown in FIGS. 5A-5C and described below refer to IMD 10B, which is implanted in the chest of patient 2. In other examples, such as IMD 10 as shown in FIG. 1, the device may be implanted or strapped in other locations and the process may be modified as needed for the selected location. Selecting yaw 206 as the first angle of rotation, which for the selected coordinate convention of this disclosure, is defined as the rotation angle around the long y-axis of IMD 10B, as depicted in FIG. 5C. Yaw 206 is used to align the device so that that the x-axis of the device is parallel to the surface of the skin at the implant site. In the illustrated example, the y-axis is still parallel to the spine and the plane of IMD 10B is not yet parallel to the plane of the implant. This orientation may be referred to as the "yawed IMD" orientation.

In some examples, pitch 204 is selected as the second angle of rotation, as depicted in FIG. 5B. The pitch angle corresponds to the angle of rotation around the x-axis of the IMD 10B to have the orientation of the x-y plane of the "yawed IMD" such that it is perfectly parallel to the surface of the skin at the center of the implant site. During this rotation, the x-axis of the yawed IMD remains parallel to the plane of the waist of the patient, and if the patient were standing upright the x-axis of the yawed and "pitched IMD" orientation is still parallel to the ground.

By defining the yaw angle followed by defining the pitch angle 204, the plane of the implant site, based on the direction of orientation vector 205A, has now been defined by these two rotations. The implant plane is parallel to orientation vector 205A and the x-axis of the implant plane is still parallel to the waist of the patient, as depicted in FIGS. 5A and 5C. The third and final angle of rotation, roll, corresponds to the rotation about the central anterior/posterior z-axis of the device in place at the center of the implant site, as depicted in FIG. 5A.

In accordance with the techniques of the disclosure, IMD 10B automatically detects and calibrates a reference orientation within patient 2. When IMD 10B is implanted in patient 2, a clinician may initially calibrate a reference orientation of IMD 10B with respect to the body of patient 2. Subsequently, as patient 2 changes body posture, the orientation of a body part of patient 2, and an orientation of IMD 10B, may change. IMD 10B may detect such changes in the orientation of IMD 10B and use such information to determine changes in an orientation of a body part or changes in a body posture of patient 2 for monitoring patient parameters or controlling delivery of therapy. However, over time, IMD 10B may shift or rotate within patient 2. This may induce error in the posture detection operations performed by IMD 10B, because a reference point used by IMD 10B may only remain valid as long as the relative position of IMD 10B with respect to patient 2 remains stable. Accordingly, over time, accumulated shifting, rotation, or other movement of IMD 10B may require recalibration of IMD 10B to account for the new position and/or orientation of IMD 10B. As described herein, IMD 10B automatically recalibrates a reference orientation for using in performing posture detection, even as the position and/or orientation of IMD 10B changes within the body of the patient.

Figure 6:
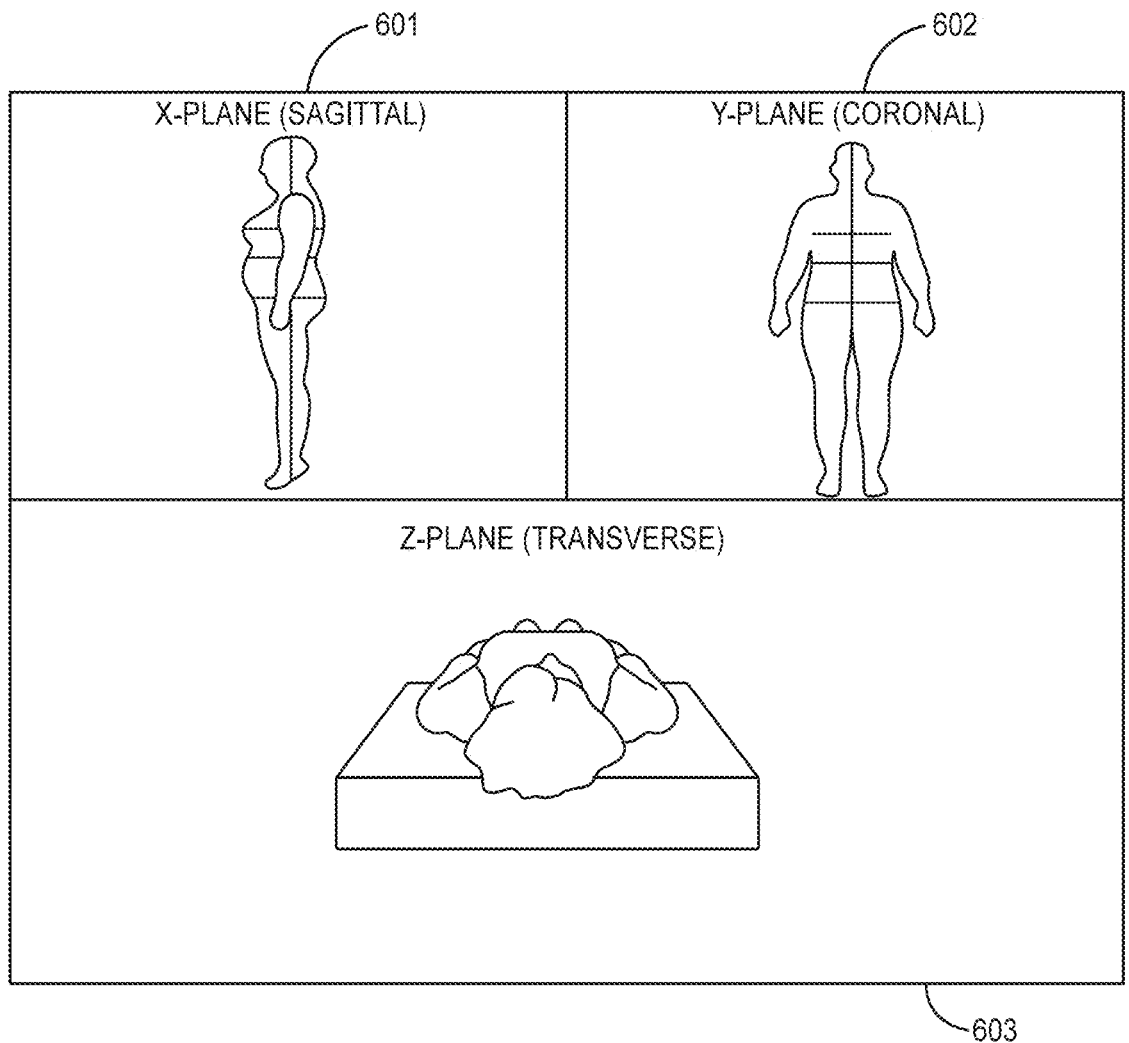
FIG. 6 are conceptual diagrams illustrating examples of a sagittal plane, a coronal plane, and a transverse plane of a patient.

FIG. 6 are conceptual diagrams illustrating examples of a sagittal plane 601, a coronal plane 602, and a transverse plane 603 of a patient. Planes 601, 602, and 603 are depicted inf FIG. 6 as perpendicular to the reader's gaze. Sagittal plane 601 is an conceptual plane that divides the body of patient 2 into a left half and a right half. Coronal plane 602 is an conceptual plane that divides the body of a patient into a front half and a back half. Transverse plane 603 is an conceptual plane that divides the body of patient 2 into an upper half and a lower half.

Figure 7A:
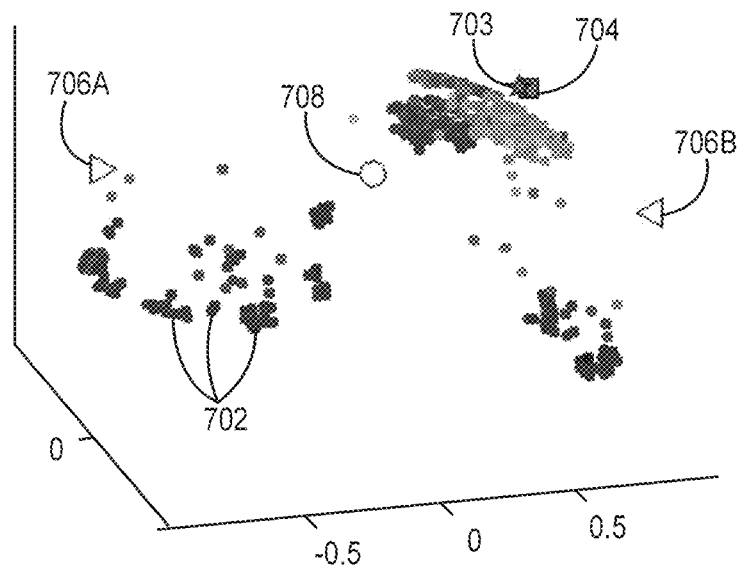
FIGS. 7A-7C are graphs depicting example sensed orientation vector data for a patient in accordance with the techniques of the disclosure.
Figure 7B:
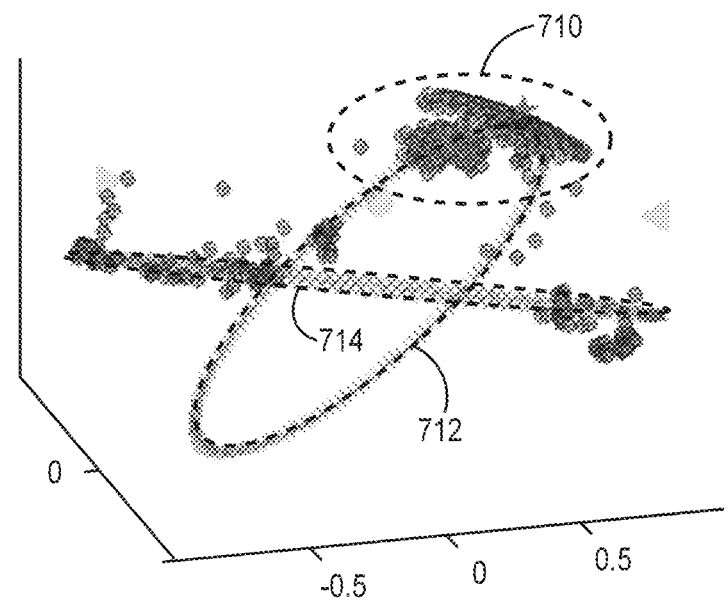
Figure 7C:
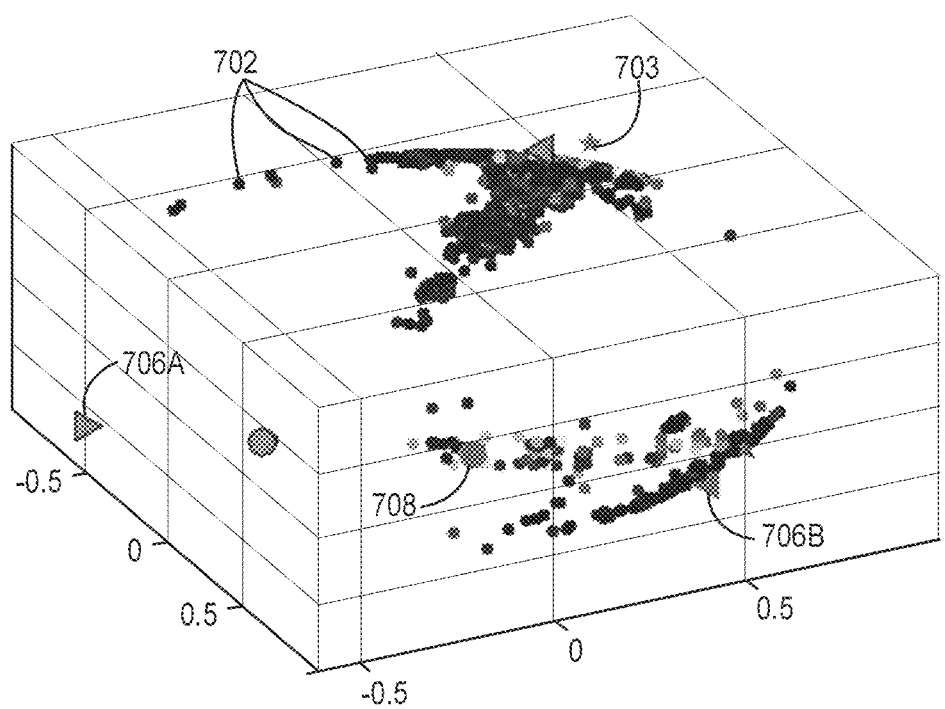

FIGS. 7A-7C are graphs depicting example sensed orientation vector data for a patient in accordance with the techniques of the disclosure. For convenience, FIGS. 7A-7C are described with respect to IMD 10 of FIG. 2. However, other medical devices, such as IMD 10A of FIG. 1 or IMD 10B of FIGS. 5A-5C, may operate as described with respect to FIGS. 7A-7C.

As depicted in FIGS. 7A-7C, orientation and activity sensor 87 senses a plurality of orientation vectors 702. The plurality of orientation vectors 702 contains a representative sampling of activity levels of patient 2, such as walking and/or active periods and sitting and/or inactive periods. In the example of FIG. 7A, the plurality of orientation vectors 702 represent 3 days of X,Y,Z accelerometer measurements of patient 2. Orientation and activity circuitry 86 may associate each orientation vector of the plurality of orientation vectors 702 with a level of activity of patient 2, as described in more detail with respect to FIG. 8. As depicted in FIGS. 7A-7C, orientation vectors 702 generally lie along sagittal plane 712 and transverse plane 714.

As described in more detail herein, orientation calibration circuitry 92 performs a clustering algorithm to identify a cluster of orientation vectors 710 associated with an upright posture of the patient. Orientation calibration circuitry 92 processes the cluster of orientation vectors 710 to identify an upright vector indicative of a standing posture of patient 2. Orientation calibration circuitry 92 processes the orientation vectors 710 to define sagittal plane 712 and transverse plane 714.

As an example for defining sagittal plane 712 and transverse plane 714, orientation calibration circuitry 92 may consider 1142 potential planes defined by their normal vectors. This may include up to 500 million possible combinations. Orientation calibration circuitry 92 constrains a distance of each plane to the upright vector. For example, considering orientation vector N, where an angle between N and the upright vector is greater than 70 degrees and less than 110 degrees, orientation calibration circuitry 92 classifies orientation vector N as belonging to a subset of orientation vectors associated with an upright posture of patient 2. Where an angle between N and the upright vector is less than 45 degrees, orientation calibration circuitry 92 classifies orientation vector N as belonging to a subset of orientation vectors associated with a recumbent posture of patient 2. Orientation calibration circuitry 92 may perform a culling operation to remove redundant upright orientation vectors. In some examples, more than 37,000 redundant combinations may be removed. Orientation calibration circuitry 92 calculates a mean squared error (MSE) of a remaining 367 planes and retains only the pairs of planes that have a low covariance of error. This may result in approximately 5,000 combinations of pairs of planes. Orientation calibration circuitry 92 uses a MSE to fit the sensed orientation vectors 702 to two planes, resulting in defined orientations for sagittal plane 712 and transverse plane 714. Once orientation calibration circuitry 92 has defined sagittal plane 712 and transverse plane 714, orientation calibration circuitry 92 classifies each of the plurality of orientation vectors 702 as belonging to a subset of orientation vectors associated with an upright posture of patient 2 or as belonging to a subset of orientation vectors associated with a recumbent posture of patient 2 based on a proximity of the orientation vector to one sagittal plane 712 and transverse plane 714.

Orientation calibration circuitry 92 may use the upright vector 703, sagittal plane 712, and transverse plane 714 to generate estimates of a posture of patient 2, such as an estimate 703 of a standing posture of patient, estimate 704 of a prone posture, estimate 706A of right lateral recumbent posture and estimate 706B of left lateral recumbent posture, or estimate 708 of a supine posture. Estimates 703, 704, 706A-706B, and 708 may subsequently be used by orientation and activity circuitry 86 as reference points for use in determining a posture of patient 2.

Figure 8:
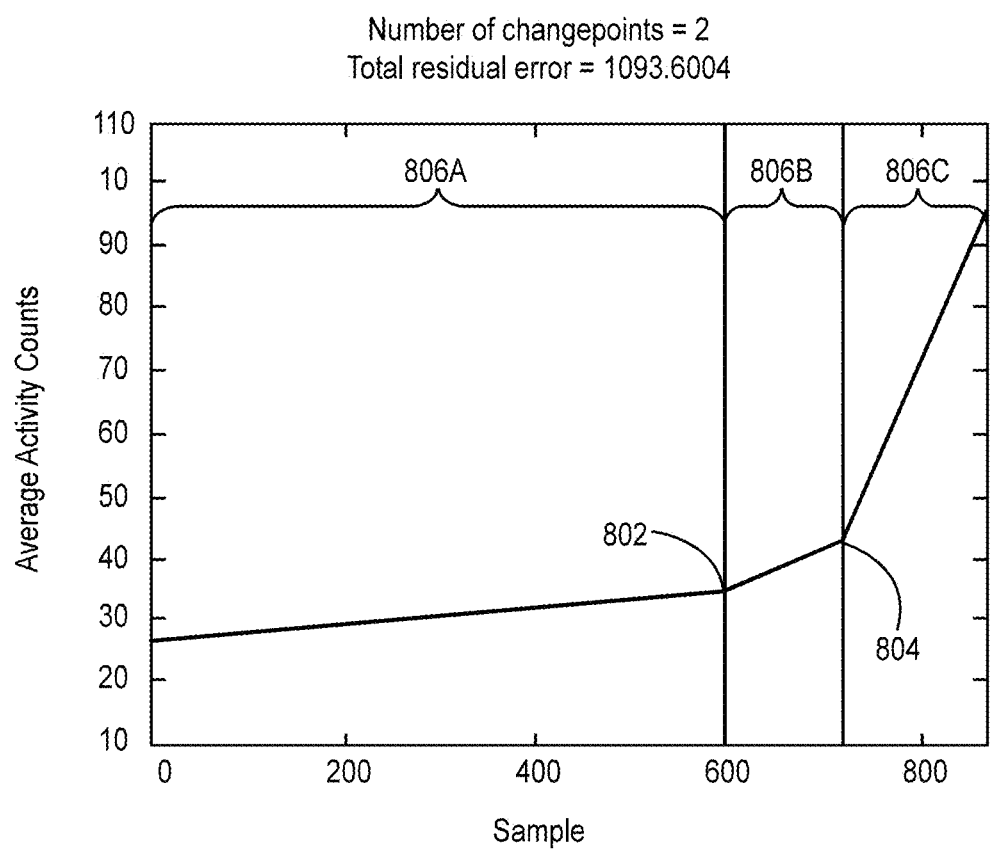
FIG. 8 is a graph depicting an example transition from a resting period to an active period for determining an upright posture vector in accordance with the techniques of the disclosure.

FIG. 8 is a graph depicting an example transition from a resting period 806A to an active period 806B for determining an upright posture vector in accordance with the techniques of the disclosure. As described above, IMD 10 may use an activity count of patient 2 to determine a level of activity of a patient. As depicted in FIG. 8, patient 2 transitions from a resting period 806A, to an active period 806B, to a strenuous active period 806C. The resting period 806A may be characterized as a low level of activity of patient 2, such as sitting, resting, or sleeping, which is expressed as a low value of an activity count. The active period 806B may be characterized as a level of activity of patient 2 that corresponds to light or medium activity, such as walking or standing, which is expressed as a medium value of an activity count. The strenuous active period 806C may be characterized as a level of activity of patient 2 that corresponds to high levels of physical exercise, such as running, jogging, or performing strenuous activity, which is expressed as a high value of an activity count. As depicted in FIG. 8, the activity count of patient 2 may exhibit two inflection points 802 and 804. Inflection point 802 occurs between resting period 806A and active period 806B, and inflection point 804 occurs between active period 806B and strenuous active period 806C. Inflection points 802 and 804 may be determined by a clinician and used to define a predetermined threshold for orientation and activity circuitry 86 to determine an activity level of patient 2 associated with a particular activity count.

As described herein, IMD 10 may sense a plurality of orientation vectors for patient 2. IMD 10 may concurrently determine an activity level of patient 2 based on an activity count for patient 2. IMD 10 may associate each orientation vector of the plurality of orientation vectors 702 with the activity level of patient 2. In some examples, IMD 10 determines an upright vector for use in determining a reference orientation of IMD 10 with respect to a body of patient 2. The upright vector can be calculated from an average of the plurality of orientation vectors that correspond to active period 806B.

In some examples, periods of high activity, such as strenuous active period 806C, may be associated with artifacts. In an example implementation, accelerometers of orientation and activity sensor 87 that sense the plurality of orientation vectors may have a maximum measurable limit of −3G to +3G (where a "G" refers to 1 unit of Earth's gravity). High activity during strenuous active period 806C, such as running, jumping, climbing stairs, or posture transition, may exceed the maximum measurable limit of accelerometers of orientation and activity sensor 87, causing the accelerometers to saturate, or "rail." While the accelerometers are saturated due to high activity, values sensed by orientation and activity sensor 87 may be inaccurate or subject to error, leading to poor estimates of posture of patient 2.

To reduce the likelihood that periods of high activity cause error in the calculated average of the plurality of orientation vectors, IMD 10 may apply a high-activity filtering operation to the sensed plurality of orientation vectors for patient 2. For example, IMD 10 may reject orientation vectors that are sensed concurrently with periods of high activity, such as strenuous active period 806C. Thus, IMD 10 may use only orientation vectors sensed concurrently with a "sweet" zone of activity levels for calculating the upright vector of patient 2 and/or the posture of patient 2.

IMD 10 may implement a high-activity filtering operation to reject orientation vectors that are sensed concurrently with periods of high activity as described herein in numerous ways. For example, IMD 10 may apply a simple absolute or relative threshold to determined activity levels to reject orientation vectors sensed concurrently with activity that exceed the threshold. The threshold may be, for example, a maximum value for an activity count or a maximum value for raw data sensed by an accelerometer of orientation and activity sensor 87. As another example, IMD 10 may reject an orientation vector sensed concurrently with an instance of "railing" or saturation of an accelerometer of orientation and activity sensor 87.

As yet a further example, IMD 10 may apply more complex formulae to reject orientation vectors that are sensed concurrently with periods of high activity. As an example implementation, IMD 10 determines an activity count for an activity count integration window. IMD 10 determines a temporal stability of an orientation vector sensed concurrently with the activity count integration window. IMD 10 may reject orientation vectors that exhibit low temporal stability during the activity count integration window, such as a temporal stability that is less than a predetermined threshold. For example, IMD 10 applies a low-pass filter to sensed X,Y,Z accelerometer values of orientation and activity sensor 87. IMD 10 applies a mathematical function to the sensed X,Y,Z accelerometer values to determine a variance of the sensed X,Y,Z accelerometer values. The mathematical function may include, for example, a large linear trend, maximum-minimum value, sum of absolute differences, or other function. IMD 10 rejects orientation vectors sensed concurrently with sensed X,Y,Z accelerometer values of orientation and activity sensor 87 that exhibit high variance.

Thus, IMD 10, in accordance with the techniques of the disclosure, may use an adaptive algorithm to automatically identify anatomical planes of patient 2 using sensor measurements. The sensor measurements may, for example, be accelerometer measurements from one or more 3-axis accelerometers located within IMD 10, an external device such as external device 10 of FIG. 1, or externally affixed to a body of patient 2. The techniques of the disclosure eliminate the need for a clinician to manually calibrate sensor-to-body positions of IMD 10 after implanting IMD 10.

The algorithm to automatically identify anatomical planes of patient 2 using sensor measurements executed by IMD 10 may be described as having two components. First, IMD 10 identifies an upright vector that corresponds to an upright posture of patient 2. Second, IMD 10 classifies a plurality of orientation vectors sensed for patient 2 as indicative of a posture of patient 2, such as upright, prone, supine, left lateral recumbent, or right lateral recumbent.

IMD 10 may identify the upright vector that corresponds to an upright posture of patient 2 in different ways. As one example, IMD 10 uses an activity count to identify the upright vector. In this example, IMD 10 senses a plurality of X,Y,Z accelerometer measurements, described herein as "orientation vectors," that correspond to periods of high activity of patient 2. IMD 10 applies a low-pass filter to the accelerometer measurements and averages the measurements together over one or more days to obtain an average vector. IMD 10 uses the average vector as the upright vector. As described herein, "high activity" is defined as an integrated activity count values greater than an active threshold, such as one of inflection points 802, 804 of FIG. 8.

The integration period of the activity count may range from about 2 seconds to about 5 minutes. The specificity to upright activities are assumed to peak at durations corresponding to a minimum length of sustained activities of about 10 seconds. Longer duration activities may be obtained by summing consecutive 2 second activity periods. IMD 10 averages the low-passed accelerometer measurements over the same integration window as the activity count. Thus, each N-second activity summation corresponds to an N-second orientation vector mean.

In some examples, IMD 10 averages the activity counts and the orientation vectors continuously (e.g., via an Infinite impulse response (IIR) filter with an appropriate time constant), daily, or every N days. IMD 10 may receive feedback from a clinician or patient 2 with respect to the threshold for detecting an active period of patient 2 so as to raise or decrease a detection sensitivity for active periods of patient 2, given a number of detected events per minute or per day.

As another example, IMD 10 uses a step count or detection of walking by patient 2 to identify the upright vector. In this example, IMD 10 senses a plurality of X,Y,Z accelerometer measurements that correspond to periods of detected walking by patient 2. IMD 10 applies a low-pass filter to the accelerometer measurements and averages the measurements together over one or more days to obtain an average vector. IMD 10 uses the average vector as the upright vector. IMD 10 may detect walking, for example, via step detection algorithms applied to raw accelerometer or integrated activity counts. For example, IMD 10 may interpret a consistent pattern in a 2-second integrated activity count over several periods as corresponding to "walking" with a high degree of specificity.

IMD 10 may average multiple periods of walking continuously (e.g., via an Infinite impulse response (IIR) filter with an appropriate time constant), daily, or every N days. IMD 10 may receive feedback from a clinician or patient 2 with respect to the threshold for detecting a period of walking so as to raise or decrease a detection sensitivity for the walking periods of patient 2, given a number of detected events per minute or per day.

As another example, IMD 10 identifies the upright vector by interfacing with an external device, such as external device 10 of FIG. 1, to confirm a detected posture of patient 2. For example, IMD 10 updates a computed upright vector in accordance with a contemporaneous, low-pass filtered accelerometer measurement in response to receiving a communication from external device 10 that confirms that patient 2 is (or was previously) upright at a specific time. In some examples, the upright vector is a weighted mean of a plurality of accelerometer measurements, each accelerometer measurement coincident with a time, as confirmed by external device 10, that patient 2 was upright. For example, external device 10 may be a vehicle that confirms patient 2 is in a seated posture (e.g., while driving), a body scale that confirms patient 2 is standing on the scale, an application executing on a mobile device that initiates periodic, guided calibrations with patient 2, or a mobile device that detects walking via step detection software and confirms patient 2 is assuming a standing or walking posture.

IMD 10 may use multiple methods to classify the plurality of orientation vectors sensed for patient 2 as indicative of a posture of patient 2. As one example, IMD 10 may classify orientation vectors as indicative of a posture of patient 2 based on an angle formed by each orientation vector with the computed upright vector. IMD 10 senses orientation vectors for patient 2 according to a periodic scale, such as every 2 seconds, every 5 minutes, etc. IMD 10 may interpret an orientation vector as indicative of an upright posture if an angle formed by the orientation vector with the upright vector is less than or equal to a predetermined upright angle. IMD 10 may interpret an orientation vector as indicative of a recumbent posture if the angle formed by the orientation vector with the upright vector is greater than the predetermined upright angle. In some examples, the predetermined upright angle is 20 degrees. In some examples, the predetermined upright angle is 45 degrees.

While the use of the angle formed by the orientation vector with the upright vector to indicate posture may be simple to implement, this method may only be able to determine whether patient 2 is upright or recumbent. Additional granularity in the posture of patient 2 is desirable to perform more accurate patient parametric data monitoring and/or therapy delivery.

As another example, IMD 10 may classify orientation vectors as indicative of a posture of patient 2 based on a proximity of the orientation vectors to one of two planes (e.g., a sagittal plane and a transverse plane) fitted to the sensed orientation vectors. In this example, IMD 10 stores all or a subset of the orientation vectors (e.g., means of low-pass filtered, X,Y,Z accelerometer measurements) and corresponding activity values. Both the orientation vectors and activity values are calculated over the same N time intervals and oversampled over several days. In some examples, the orientation vectors and activity value data is stored external to IMD 10, such as a cloud computing infrastructure, or in one of external server 164 and computing devices 170 of FIG. 4.

IMD 10 fits a transverse plane to a cluster of orientation vectors associated with an upright posture of patient 2. As described herein, the terms transverse plane and "upright plane" may be used interchangeably. As an example, to reduce the number of orientation vectors required for analysis, IMD 10 down-samples the plurality of sensed orientation vectors by associating each vector with a grid element on a sphere. In some examples, IMD 10 tracks a number of vectors for each grid element. IMD 10 retains only the grid elements with at least one associated orientation vector. IMD 10 classifies all grid elements within a predetermined upright angle of the upright vector as belonging to a subset of grid elements. In some examples, the predetermined upright angle is 20 degrees.

IMD 10 applies a clustering algorithm to dilate the subset of grid elements into a cluster of grid elements that include nearby neighbors. In some examples, the cluster of grid elements have an angle separation that is less than 10 degrees from a grid element of the subset of grid elements. In some examples, IMD 10 retains only the grid elements of the cluster of grid elements that have having no more than 1 additional observation than the grid element within the cluster of grid elements to which the grid element is compared. This constraint mitigates merging of distinct clusters (e.g., the clustering algorithm is restricted from moving from areas of low population to areas of dense population. The long axis of the resulting cluster of grid elements typically falls along the transverse plane because a torso of patient 2 typically rotates to a greater degree front-to-back than side-to-side during normal activities of daily living.

IMD 10 calculates a main axis of variation within the cluster of grid elements by determining an eigenvector having the largest eigenvalue. IMD 10 weights the covariance matrix of the cluster of grid elements by the number of corresponding orientation vectors (e.g., a number of associated observations). IMD 10 calculates a normal vector to the transverse plane via the cross product of the upright vector with the main eigenvector. The normal vector to the transverse plane is perpendicular to the transverse plane and may be considered to define an orientation of the transverse plane.

The resulting vector approximately points towards one of two mean posture vectors (e.g., left lateral recumbent or right lateral recumbent). To unambiguously classify recumbent postures, the normal vector to the transverse plane must point towards a single known vector. As an arbitrary convention used herein, this known vector is selected as the right lateral recumbent. However, the left lateral recumbent may also be used. In other words, the eigenvector is assumed to point towards a mean supine vector of patient 2.

IMD 10 may assign a correct polarity to the transverse plane by enforcing an assumption that leaning-back postures (e.g., towards a supine position) are more prevalent than forward-leaning postures (e.g., towards a prone position). IMD 10 projects grid elements that are: 1) outside of the upper cluster of grid elements; and 2) less than 45 degrees from the transverse plane onto the transverse plane. A mean of these projections, weighted by the number of corresponding orientation vectors, points toward the more prevalent of the two leaning/lying postures, which the techniques of the disclosure assume to be a supine position. IMD 10 fixes the polarity of the normal vector of the transverse plane by recalculating the normal vector via the cross product of the upright vector with the preferred lying vector.

Furthermore, IMD 10 fits a sagittal plane to the orientation vectors not included within the cluster of grid elements associated with the upright posture of patient 2. As described herein, the terms sagittal plane and "lying plane" may be used interchangeably. IMD 10 classifies each orientation vector that is not included within the cluster of grid elements associated with the upright posture of patient 2 as belonging to a second subset of orientation vectors. IMD calculates a cross product of each orientation vector of the second subset of orientation vectors and each other orientation vector of the second subset of orientation vectors. IMD 10 flips a sign of any resulting cross product whose plane forms a negative angle to the upright vector.

The equation for obtaining the resulting cross products is set forth below, wherein n is a first orientation vector of the second subset of orientation vectors and u is a second orientation vector of the second subset of orientation vectors:

$$\sin^{-1} \frac{|\vec{n} \cdot \vec{u}|}{|\vec{n}| \cdot |\vec{u}|} < 0$$

IMD 10 calculates a weighted mean of the resulting cross products. The weighted mean is the estimated normal vector to the sagittal plane. The normal vector to the sagittal plane is perpendicular to the sagittal plane and may be considered to define an orientation of the sagittal plane.

IMD 10 determines an angle of each grid element with respect to the transverse and sagittal planes. In some examples, the angle is a continuous value which IMD 10 may use to improve tracking of patient posture over time relative to discrete postures classes. For example, as a body angle of patient 2 changes during sleep from 5 degrees to 25 degrees, IMD 10 may determine that patient 2 has assumed a different posture. IMD 10 classifies individual orientation vectors as representative of a discrete posture class based on a proximity to each of the transverse and sagittal planes. In some examples, the posture classes include upright, supine, prone, left lateral recumbent and right lateral recumbent.

To associate an orientation vector with an upright posture, IMD 10 identifies those orientation vectors as indicating an upright posture with a high degree of probability. Such highly probable upright vectors are classified satisfying all of the following criteria:

$A_{OU} < 45°$ $|A_{OT} - 90°| < 45°$ $|A_{OT} - 90°| < 90° - A_{OS}$ wherein $A_{OU}$ is an angle formed by the orientation vector with the upright vector, $A_{OT}$ is an angle formed by the orientation vector with the normal vector of the transverse plane, and $A_{OS}$ is an angle formed by the orientation vector with the normal vector of the sagittal plane.

IMD 10 may expand the classification of "indicating an upright posture" to orientation vectors that are nearby the orientation vectors indicating an upright posture with a high degree of probability. For example, if the majority of orientation vectors neighboring an unclassified orientation vector are themselves classified as indicative of an upright posture, IMD 10 may classify the unclassified orientation vector as indicative of an upright posture. In some examples, two orientation vectors are considered "nearby" or "neighboring" if the two orientation vectors have an angle separation that is less than 20 degrees.

IMD 10 may classify the remaining unclassified orientation vectors according to recumbent postures. For example, IMD 10 projects the remaining unclassified orientation vectors onto the sagittal plane. IMD 10 calculates an estimated supine vector from a cross product of the normal vector of the transverse plane with the normal vector of the sagittal plane. IMD 10 projects the estimated supine vector onto the sagittal plane. IMD 10 calculates, for each of the projected orientation vectors, an angle of the projection to an angle of the supine vector projection.

If the angle between an orientation vector projected onto the sagittal plane and the supine vector projection is less than 45 degrees, IMD 10 classifies the orientation vector as indicative of a supine posture. If the angle between an orientation vector projected onto the sagittal plane and the supine vector projection is greater than 135 degrees, IMD 10 classifies the orientation vector as indicative of a prone posture.

If the angle between an orientation vector projected onto the sagittal plane and the supine vector projection is greater than or equal to 45 degrees and less than or equal to 135 degrees, and if the angle between the orientation vector and the transverse plane is less than 0 degrees, IMD 10 classifies the orientation vector as indicative of a left lateral recumbent posture. If the angle between an orientation vector projected onto the sagittal plane and the supine vector projection is greater than or equal to 45 degrees and less than or equal to 135 degrees, and if the angle between the orientation vector and the transverse plane is greater than or equal to 0 degrees, IMD 10 classifies the orientation vector as indicative of a right lateral recumbent posture. The relationship between angle between the orientation vector and the transverse plane and the left or right lateral recumbent posture is described by the following equation:

$$\sin^{-1}\frac{|\vec{n}\cdot\vec{u}|}{|\vec{n}|\cdot|\vec{u}|} < 0$$

Accordingly, using the foregoing method, IMD 10 may automatically calibrate a reference orientation of IMD 10 within patient 2 as well as accurately detect a posture of patient 2 without the need for periodic, manual recalibration.

FIGS. 9A-9H are graphs illustrating example patient posture data obtained in accordance with the techniques of the disclosure. As depicted in FIGS. 9A-9H, an IMD similar to IMD 10A of FIG. 1, IMD 10 of FIG. 2, or IMD 10B of FIGS. 5A-5C was implanted within 49 subjects and the techniques of the disclosure were studied. 3 reference datasets were recorded per subject. Each reference dataset was separated by 1 to 3 months and included standing, supine, left lateral recumbent, and right lateral recumbent postures. The IMD recorded raw X,Y,Z accelerometer values every 5 minutes from each subject. The raw accelerometer values were calibrated and normalized to unit orientation vectors for this study. Further, the implanted IMD recorded a mean and maximum activity count every 5 minutes for each subject. The IMD used 3 days of accelerometer data to estimate a reference orientation of the IMD with respect to the subject. The actual orientations were measured and compared to the reference orientations estimated by the IMD from the date of transmission.

Figure 9A:
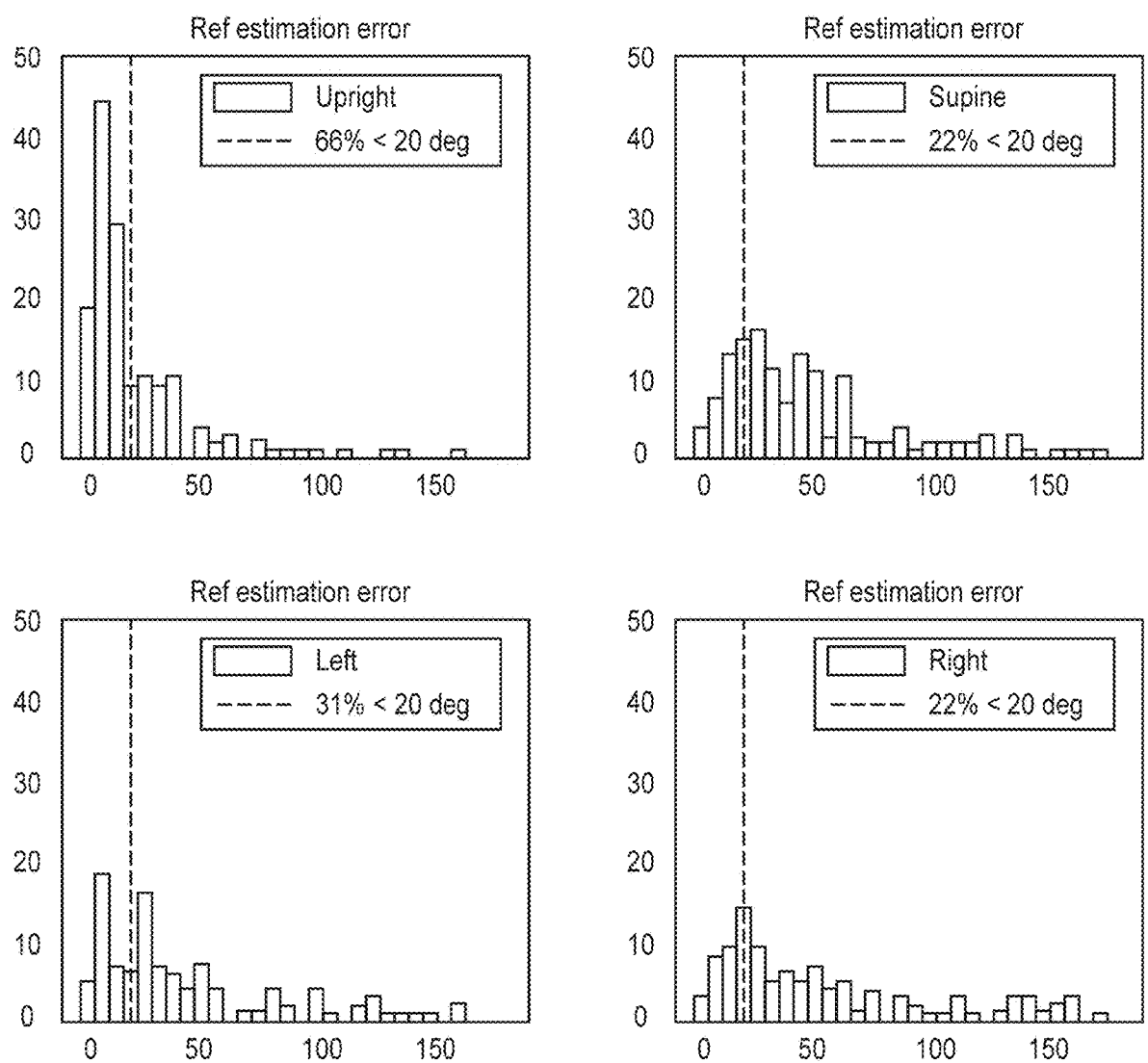
FIGS. 9A-9H are graphs illustrating example patient posture data obtained in accordance with the techniques of the disclosure.

FIG. 9A is a graph illustrating an estimation error between a measured orientation compared to a reference orientation estimated by the IMD. FIG. 9A depicts the error in reference orientation for reference orientation vectors estimated for an upright, supine, left lateral recumbent, and right lateral recumbent posture.

Figure 9B:
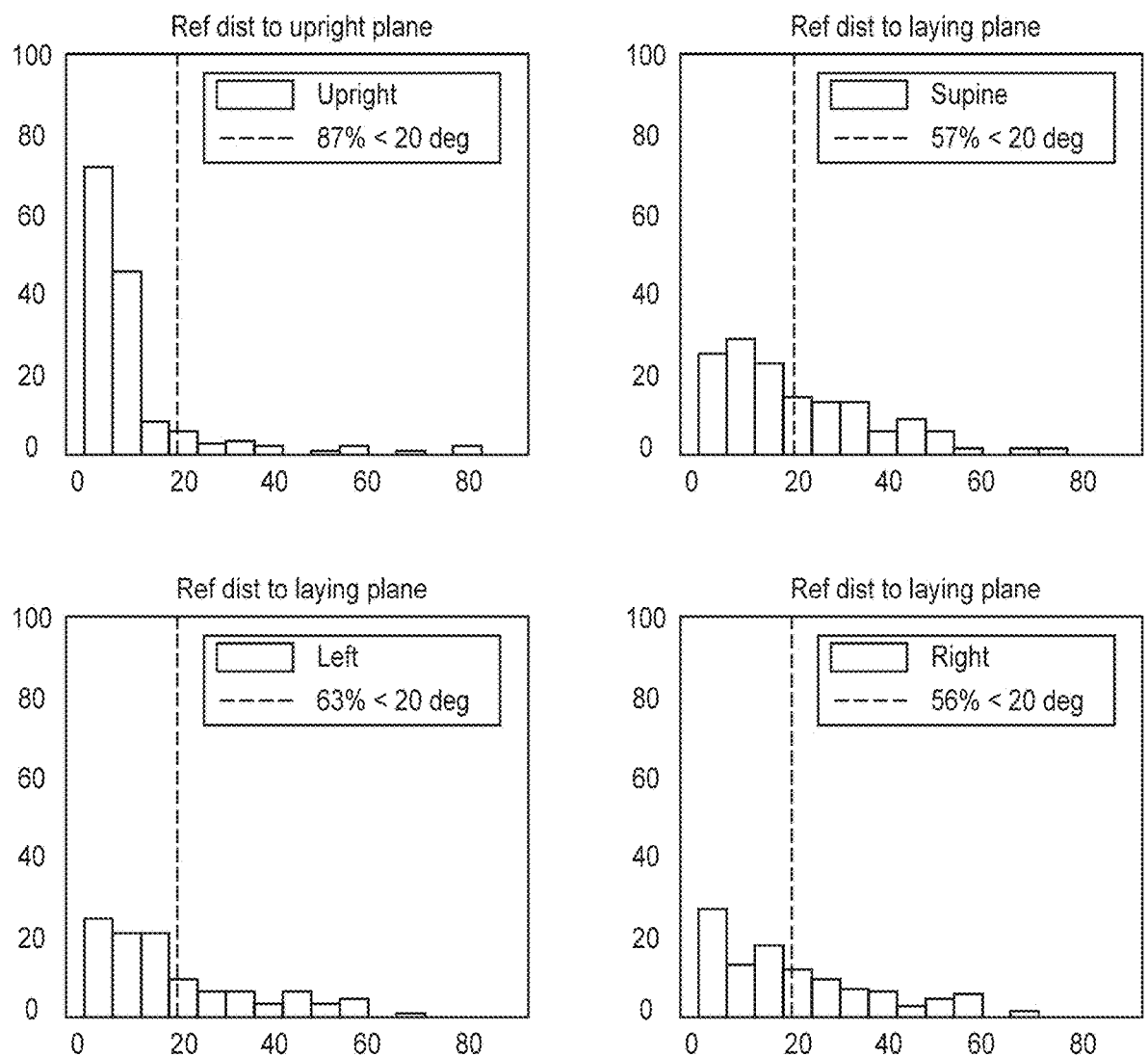

FIG. 9B is a graph illustrating a distance of a reference orientation estimated by the IMD to a transverse (e.g., upright) plane or a sagittal (e.g., laying) plane. FIG. 9A depicts a distance of an upright reference orientation to a transverse (e.g., upright) plane, a supine reference orientation to a sagittal (e.g., laying) plane, a left lateral recumbent reference orientation to a sagittal (e.g., laying) plane, and a right lateral recumbent reference orientation to a sagittal (e.g., laying) plane.

Figure 9C:
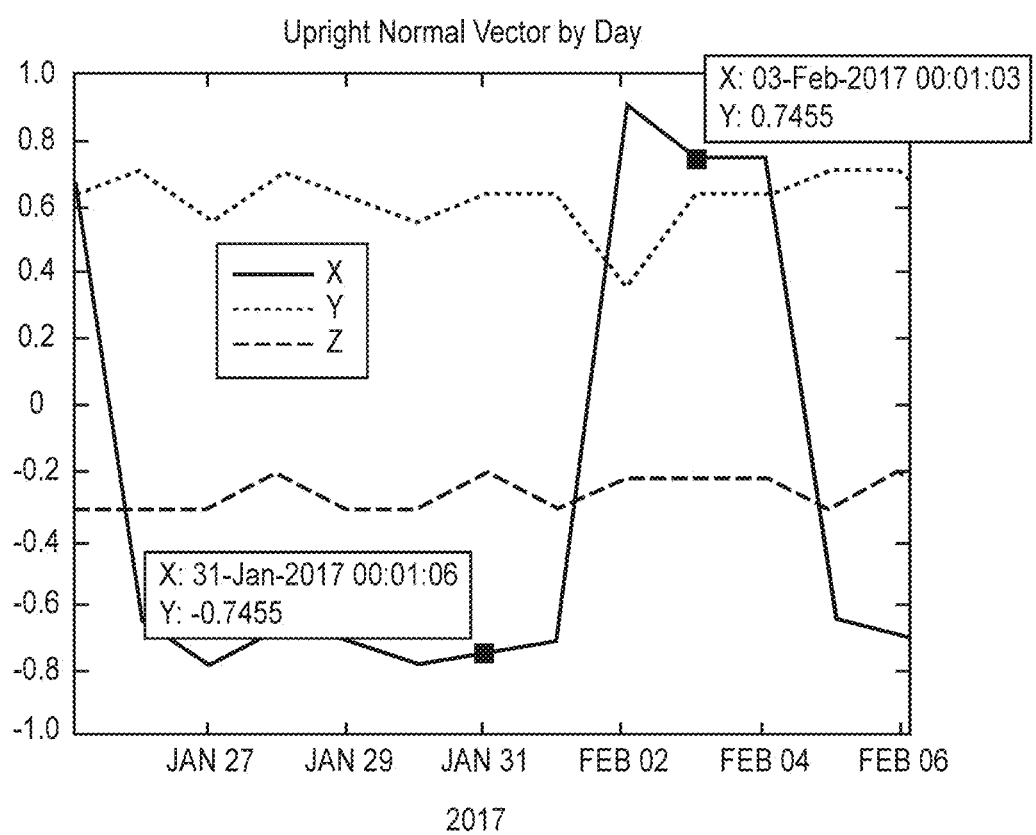

FIG. 9C is a graph illustrating an upright normal orientation vector in accordance with the techniques of the disclosure. Specifically, FIG. 9C illustrates X,Y,Z values of an estimated upright vector for subjects over a period of time. One may infer from FIG. 9C that the X-component of the estimated upright vector changes over time as a position of the IMD within the subject changes over time.

Figure 9D:
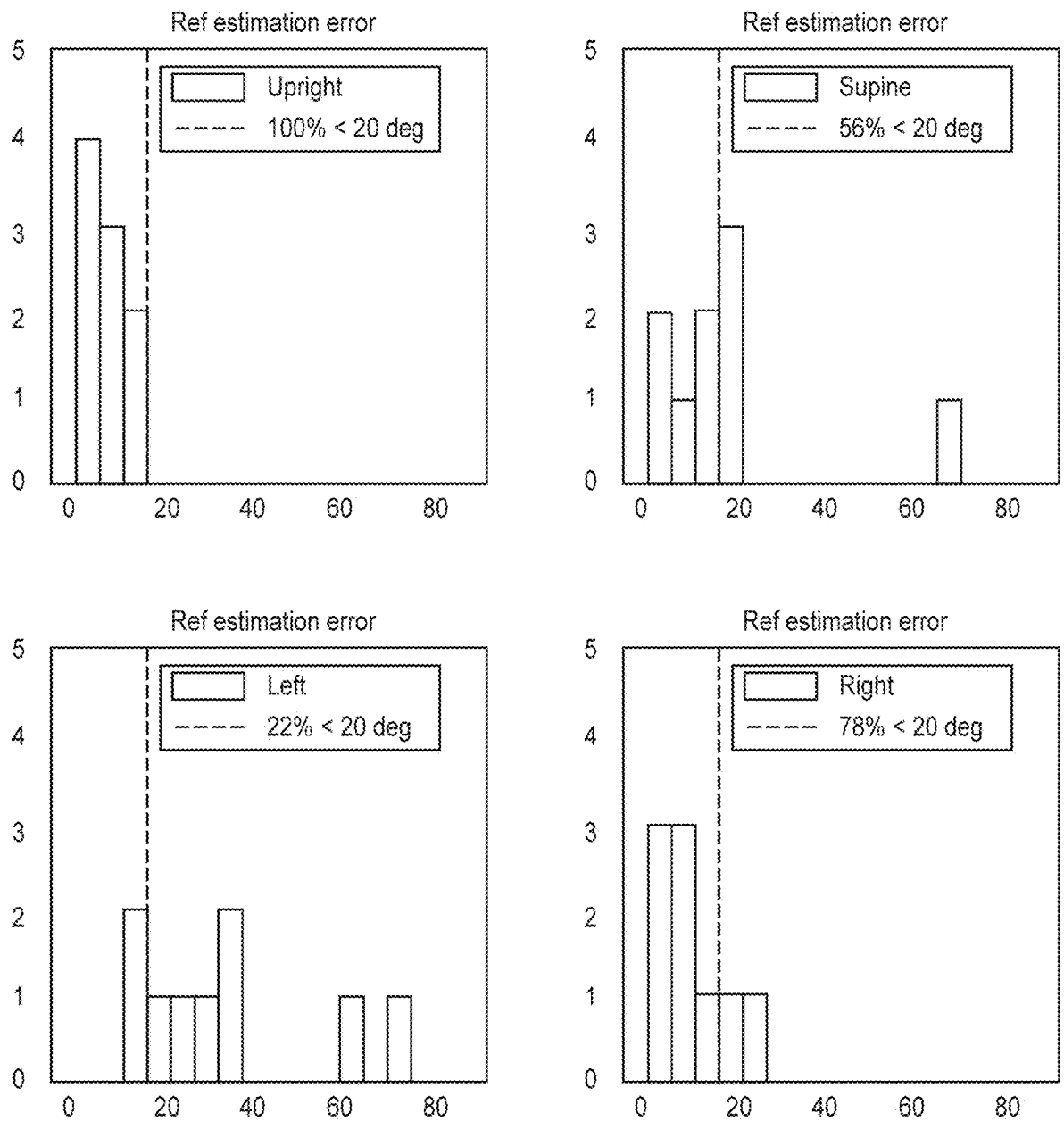
Figure 9E:
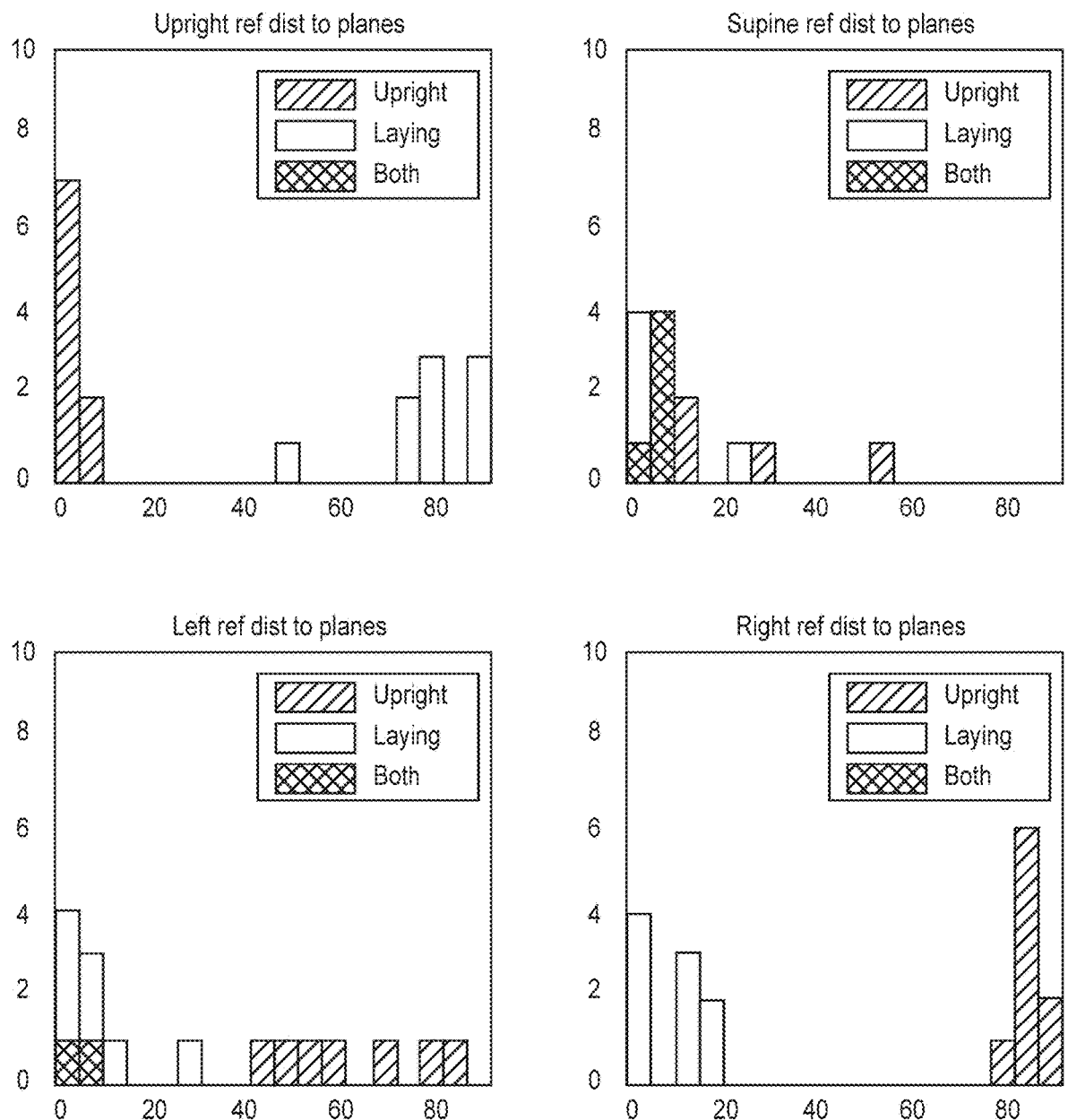

FIGS. 9D and 9E illustrate simulated data from 9 healthy subjects converted to a 1-minute sampling period. FIGS. 9D and 9E represent about 20 hours of sampling time per subject, including a sleep period. As depicted in FIGS. 9D and 9E, rotation planes estimated by an IMD operating in accordance with the techniques of the disclosure may discriminate well between body positions.

FIG. 9D is a graph illustrating an estimation error between a measured orientation compared to a reference orientation estimated by the IMD. FIG. 9D depicts the error in reference orientation for reference orientation vectors estimated for an upright, supine, left lateral recumbent, and right lateral recumbent posture.

FIG. 9E is a graph illustrating a distance of a reference orientation estimated by the IMD to a transverse (e.g., upright) plane and a sagittal (e.g., laying) plane. FIG. 9E depicts a distance of an upright reference orientation to the transverse and sagittal planes, a supine reference orientation to the transverse and sagittal planes, a left lateral recumbent reference orientation to the transverse and sagittal planes, and a right lateral recumbent reference orientation to the transverse and sagittal planes.

Figure 9F:
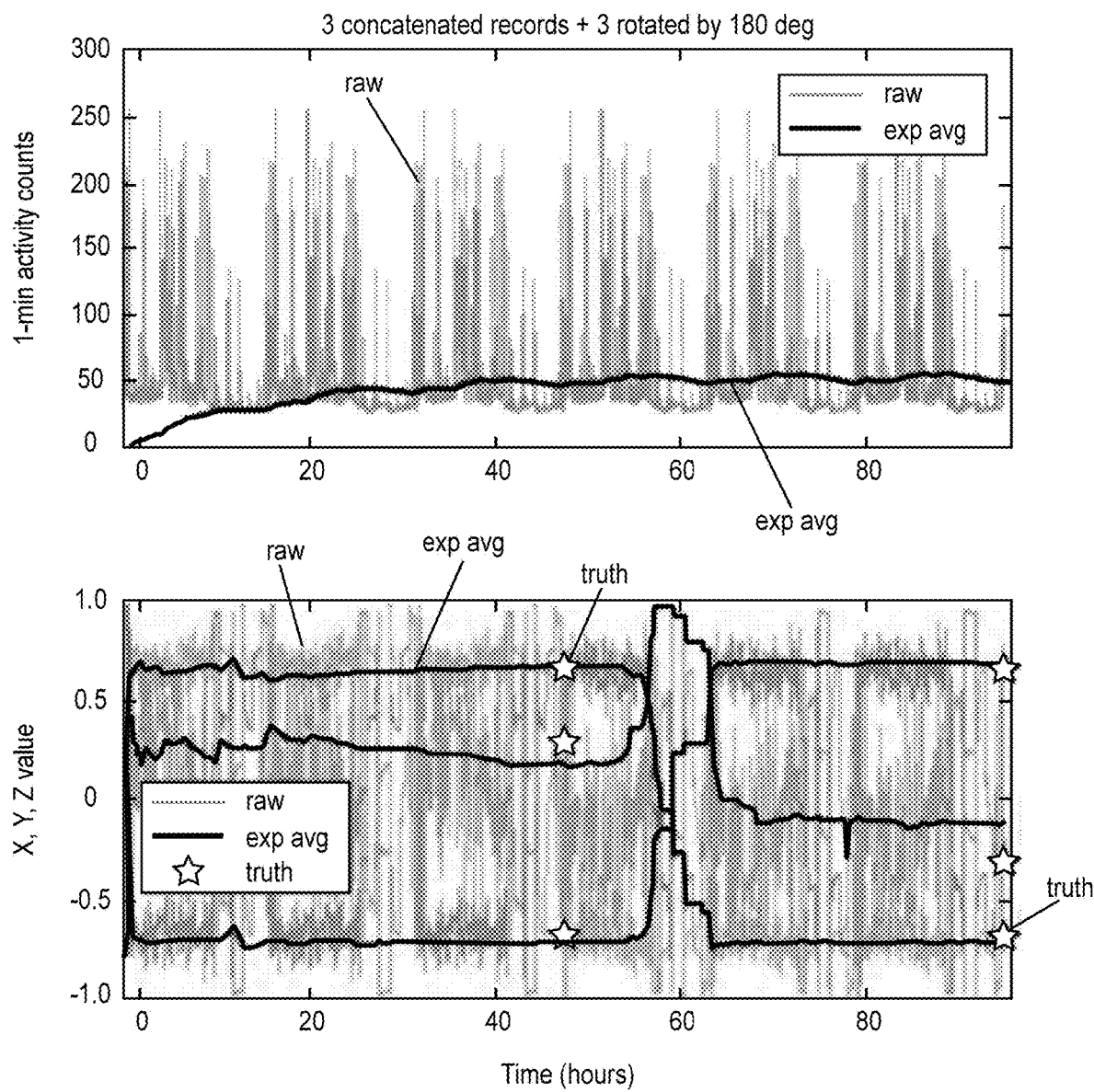

FIG. 9F is a graph illustrating an activity count of a simulated patient compared with X,Y,Z values of an estimated upright vector for a subject.

Figure 9G:
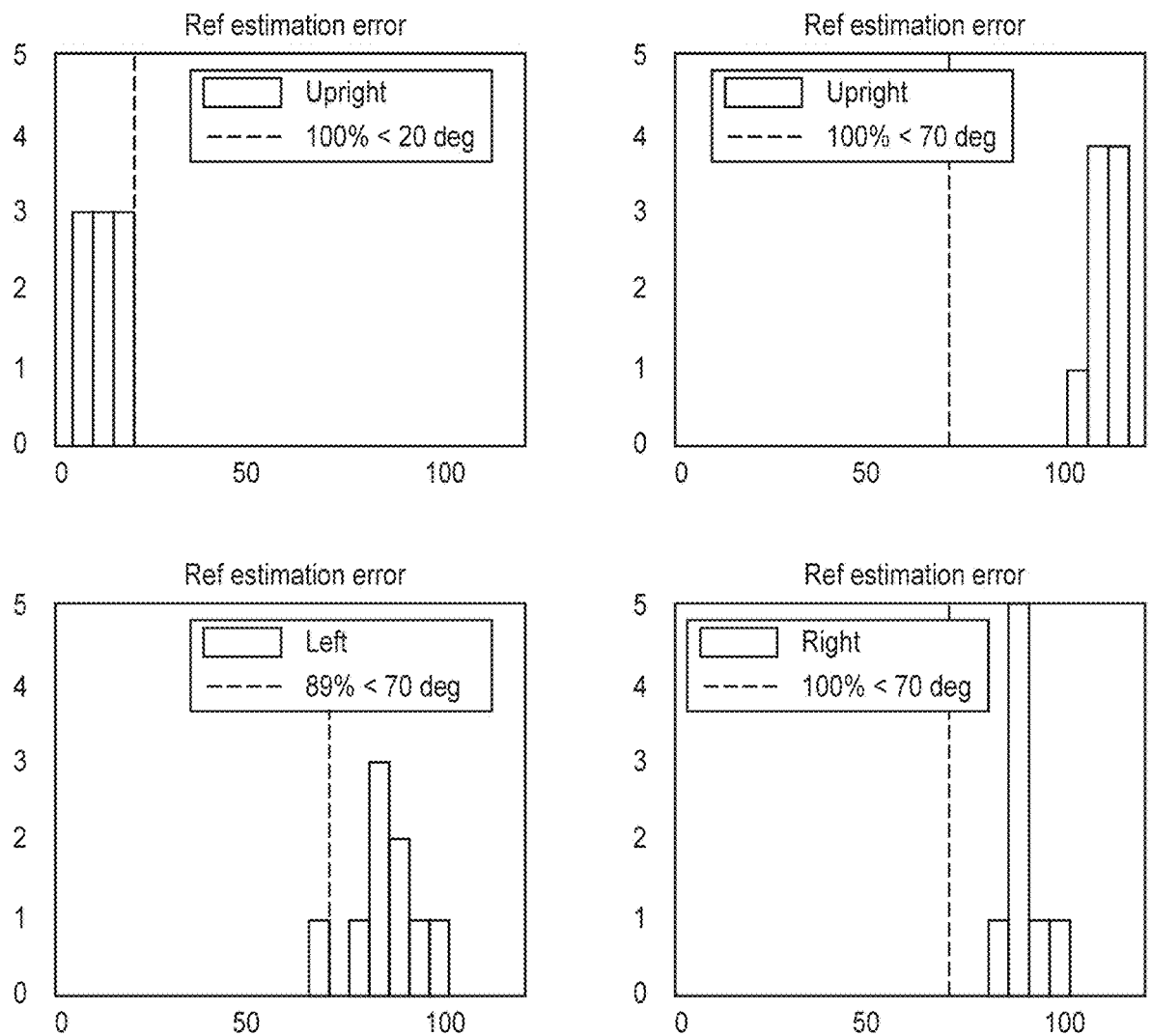

FIG. 9G is a graph illustrating a distance of a reference orientation estimated by the IMD to a transverse (e.g., upright) plane or a sagittal (e.g., laying) plane. FIG. 9G depicts a distance of an upright reference orientation to a transverse (e.g., upright) plane, a supine reference orientation to a sagittal (e.g., laying) plane, a left lateral recumbent reference orientation to a sagittal (e.g., laying) plane, and a right lateral recumbent reference orientation to a sagittal (e.g., laying) plane.

Figure 9H:
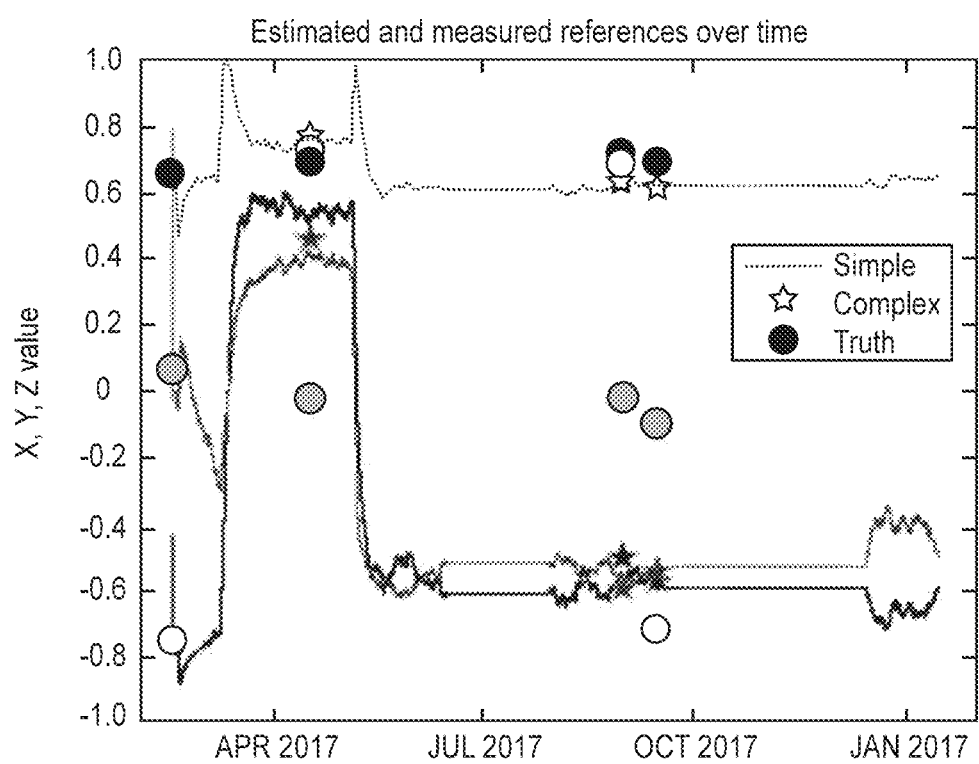

FIG. 9H is a graph illustrating reference orientations estimated by an IMD as compared with a measured orientation of the IMD. FIG. 9H depicts a correlation between several types of methods for estimating the reference orientation of IMD 10. As depicted in FIG. 9H, the estimated upright vectors are highly correlated with one another (e.g., r=0.95). Further, the estimated upright vectors correlate well with the measured reference orientations, For example, an exponential average was determined to be r=0.82 and a changepoint threshold was determined to be r=0.80.

Therefore, the techniques of the disclosure may allow an IMD to estimate planes of rotation of a body of a patient so as to obtain accurate estimations of multiple body postures. While in some examples, a moving average of the upright vector as described above may be sufficient to estimate a reference vector for an upright posture of the patient, the more complex methods for estimating reference points by fitting orientation vectors to transverse and sagittal planes described above may allow an IMD to estimate reference vectors for other postures, such as differentiating between left lateral recumbent and right lateral recumbent postures or differentiating between supine and prone postures.

Figure 10:
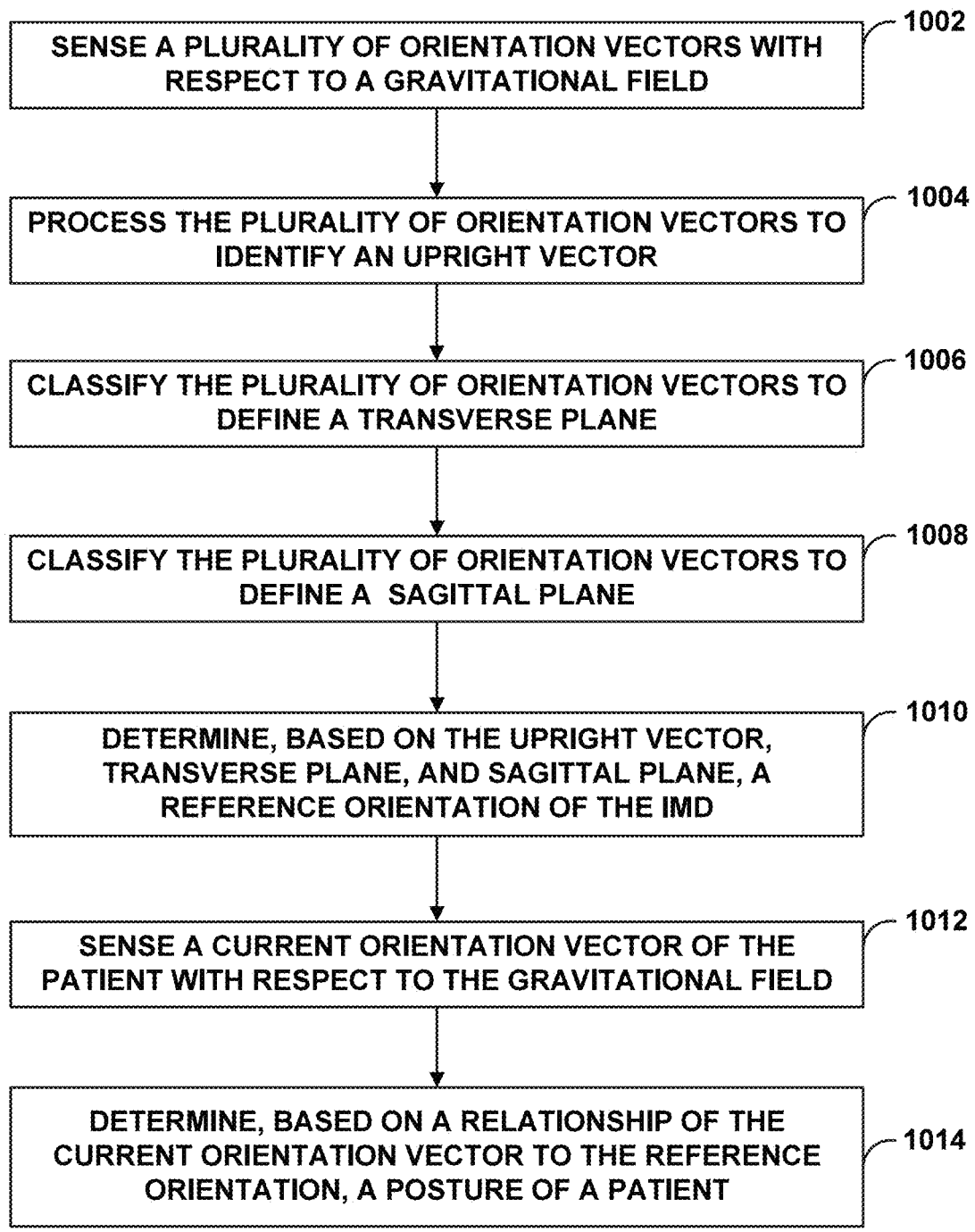
FIG. 10 is a flowchart illustrating an example operation in accordance with the techniques of the disclosure.

FIG. 10 is a flowchart illustrating an example operation in accordance with the techniques of the disclosure. For convenience, the operation of FIG. 10 is described with respect to IMD 10A of FIG. 1. However, the operation of FIG. 10 may be performed by other medical devices, such as IMD 10 of FIG. 2 or IMD 10B of FIGS. 5A-5C. Additionally, the operation of FIG. 10 may be performed, at least in part, by a computing device, e.g., external device 12, in communication with the IMD, or by processing and other circuitry described herein of any one or more devices in coordination.

IMD 10A senses, over a period of time, a plurality of orientation vectors with respect to a gravitational field (1002). Typically, each orientation vector points opposite to the direction of Earth's gravitational field. Thus, the orientation vector may be assumed to point "upward," and may be used as a point of reference to determine a current orientation of IMD 10 with respect to Earth's gravitational field. In some examples, IMD 10 includes one or more accelerometers, such as 3-axis accelerometers, capable of detecting static orientation or vectors in three-dimensions.

IMD 10A processes the plurality of orientation vectors to identify an upright vector (1004). The upright vector may correspond to an upright posture of patient 2, such as a standing or sitting posture. The techniques of the disclosure assume that a patient is in an upright position most of the time in a 24-hour period (or most of the time during daytime hours). Therefore, an average vector of the plurality of orientation vectors may be assumed to roughly correspond to an upright posture of the patient. However, the upright vector may be made more accurate by filtering a plurality of orientation vectors to obtain a set of vectors that are associated with a time of day patient 2 is expected to be active, or a high activity level of patient 2.

As one example for determining the upright vector, IMD 10A senses a plurality of orientation vectors of IMD 10A with respect to a gravitational field over a period of time. IMD 10A determines one or more orientation vectors of the plurality of orientation vectors that correspond to an activity level of patient 2 that exceeds a patient activity threshold. IMD 10A may average the one or more orientation vectors that correspond to an activity level of patient 2 that exceeds a patient activity threshold such that the average vector corresponds to the upright vector.

As another example for determining the upright vector, IMD 10A senses a plurality of orientation vectors of IMD 10A with respect to a gravitational field over a period of time. IMD 10A determines one or more orientation vectors of the plurality of orientation vectors that correspond to a walking activity of the patient. For example, IMD 10A may uses a step detector or pedometer to determine when patient 2 is walking, and select only those orientation vectors sensed concurrently with the walking activity of the patient. IMD 10A may average the one or more orientation vectors that correspond to an activity level of patient 2 that exceeds a patient activity threshold such that the average vector corresponds to the upright vector.

As another example for determining the upright vector, an external device, such as external device 12, may determine a posture of patient 2 and transmit the determined posture to IMD 10A. For example, external device 12 may receive an input from a patient indicative of a posture that patient 2 has assumed. Additionally, external device 12 may comprise a pedometer, accelerometer, or other type of sensor capable of detecting a posture of patient 12. IMD 10A senses a plurality of orientation vectors of IMD 10A with respect to a gravitational field over a period of time. IMD 10A receives, from external device 12, the determined posture of patient 2 for the sensed orientation vectors. IMD 10A determines, based on the sensed orientation vectors associated with the various postures of patient 2, one or more orientation vectors of the plurality of orientation vectors that correspond to an upright posture of the patient. IMD 10A may average the one or more orientation vectors that correspond to an activity level of patient 2 that exceeds a patient activity threshold such that the average vector corresponds to the upright vector.

IMD 10A classifies the plurality of orientation vectors to define a transverse plane (1006). IMD 10A classifies the plurality of orientation vectors with respect to the upright vector to define a transverse plane of patient 2. The transverse plane of patient 2 is a conceptual plane that roughly divides the body of patient 2 into an upper portion and a lower portion. The techniques of the disclosure assume that sensed orientation vectors sensed above and below the transverse plane of patient 2 may correspond to an upright position or a recumbent position of patient 2, respectively.

To determine the transverse plane, IMD 10A classifies determines, for each sensed orientation vector, an angle between the orientation vector and the upright vector. IMD 10A classifies compares the angle between the orientation vector and the upright vector to a predetermined upright angle. For example, the predetermined upright angle is about 20 degrees from the upright angle. If the angle between the orientation vector and the upright vector is less than the predetermined upright angle, IMD 10A classifies the respective orientation vector as one of a first subset of the plurality of orientation vectors associated with an upright posture of the patient. If the angle between the orientation vector and the upright vector is greater than or equal to the predetermined upright angle, IMD 10A classifies the respective orientation vector as one of a second subset of the plurality of orientation vectors associated with a recumbent posture of the patient. IMD 10A defines the transverse plane of the patient as a plane between the first subset of the plurality of orientation vectors associated with the upright posture of patient 2 and the second subset of the plurality of orientation vectors associated with the recumbent posture of patient 2.

Further, IMD 10A classifies the plurality of orientation vectors to define a sagittal plane of patient 2 (1008). The sagittal plane of patient 2 is an conceptual plane that roughly divides the body of patient 2 into a left half and a right half. The techniques of the disclosure assume that sensed orientation vectors sensed to the left and right of the sagittal plane of patient 2 may correspond to the patient laying on a left side or on a right side of the body (e.g., a left lateral recumbent or right lateral recumbent posture).

As one example for determining the sagittal plane, IMD 10A associates each orientation vector with a grid element of a sphere based on an angle formed by the orientation vector with respect to the upright vector. IMD 10A identifies a subset of the plurality of grid elements that form an angle with the upright vector that is less than a predetermined upright angle. In some examples, the predetermined upright angle is 20 degrees. IMD 10A applies a clustering algorithm to identify a cluster of grid elements of the plurality of grid elements that are neighbors to the subset of the plurality of grid elements. In some examples, a grid element is a neighbor of the subset of the plurality of grid elements if the grid element is offset from a grid element of the subset of the plurality of grid elements by less than 10 degrees. IMD 10A determines a main eigenvector for the cluster of grid elements. The main eigenvector comprises a higher eigenvalue than each other eigenvector of a plurality of eigenvectors of the cluster of grid elements. IMD 10A determines, based on the cross product of the upright vector with the main eigenvector, a normal vector which defines the sagittal plane of patient 2 in that the normal vector is perpendicular to the sagittal plane.

As another example for determining the sagittal plane, IMD 10A classifies each orientation vector as one of a first subset of the plurality of orientation vectors associated with an upright posture of the patient or one of a second subset of the plurality of orientation vectors associated with an recumbent posture of the patient. IMD 10A calculates a plurality of cross products between each orientation vector of the first subset of the plurality of orientation vectors associated with the upright posture of the patient and each orientation vector of the second subset of the plurality of orientation vectors associated with the recumbent posture of the patient. IMD 10A determines a weighted mean of each of the cross products to obtain a normal vector which defines the sagittal plane of patient 2.

IMD 10A determines, based on the upright vector, transverse plane, and sagittal plane, a reference orientation of IMD 10A with respect to a body of patient 2 (1010). IMD 10A senses a current orientation vector of the patient with respect to the gravitational field (1012). IMD 10A determines, based on a relationship of the current orientation vector to the reference orientation, a posture of patient 2 (1014). Generally speaking, if the orientation vector is similar to the upright vector and above the transverse plane, IMD 10A determines that patient 2 is in an upright posture. If the orientation vector is not similar to the upright vector, below the transverse plane, and located approximately along the sagittal plane, IMD 10A determines that patient 2 is in a prone or supine position. If the orientation vector is not similar to the upright vector, located approximately along the transverse plane, and to the left or right of the sagittal plane, IMD 10A determines that patient 2 is in left lateral recumbent or right lateral recumbent position. Additional details in evaluating the orientation vector with respect to the upright vector, the transverse plane and the sagittal plane are described in greater detail below.

Because of some inherent sensor inaccuracies and modeling errors, the transverse plane, as constructed by IMD 10A, may or may not be coplanar with an actual, real-world sagittal plane of patient 2. Further, the sagittal plane, as constructed by IMD 10A, may or may not be coplanar with an actual, real-world transverse plane of patient 2. Furthermore, the transverse and sagittal planes constructed by IMD 10A may not necessarily be perpendicular to one another (as the actual, real-world transverse and sagittal planes of patient 2 would be). However, an advantage of the techniques of the disclosure is that IMD 10A may still accurately calibrate an orientation of IMD 10A with respect to the body of patient 2 such that IMD 10A may accurately detect a posture of patient 2, even though the transverse and sagittal planes of patient 2 computed by orientation calibration circuitry 92 are not perpendicular to one another or coplanar with the actual, real-world transverse and sagittal planes of patient 2.

Figure 11:
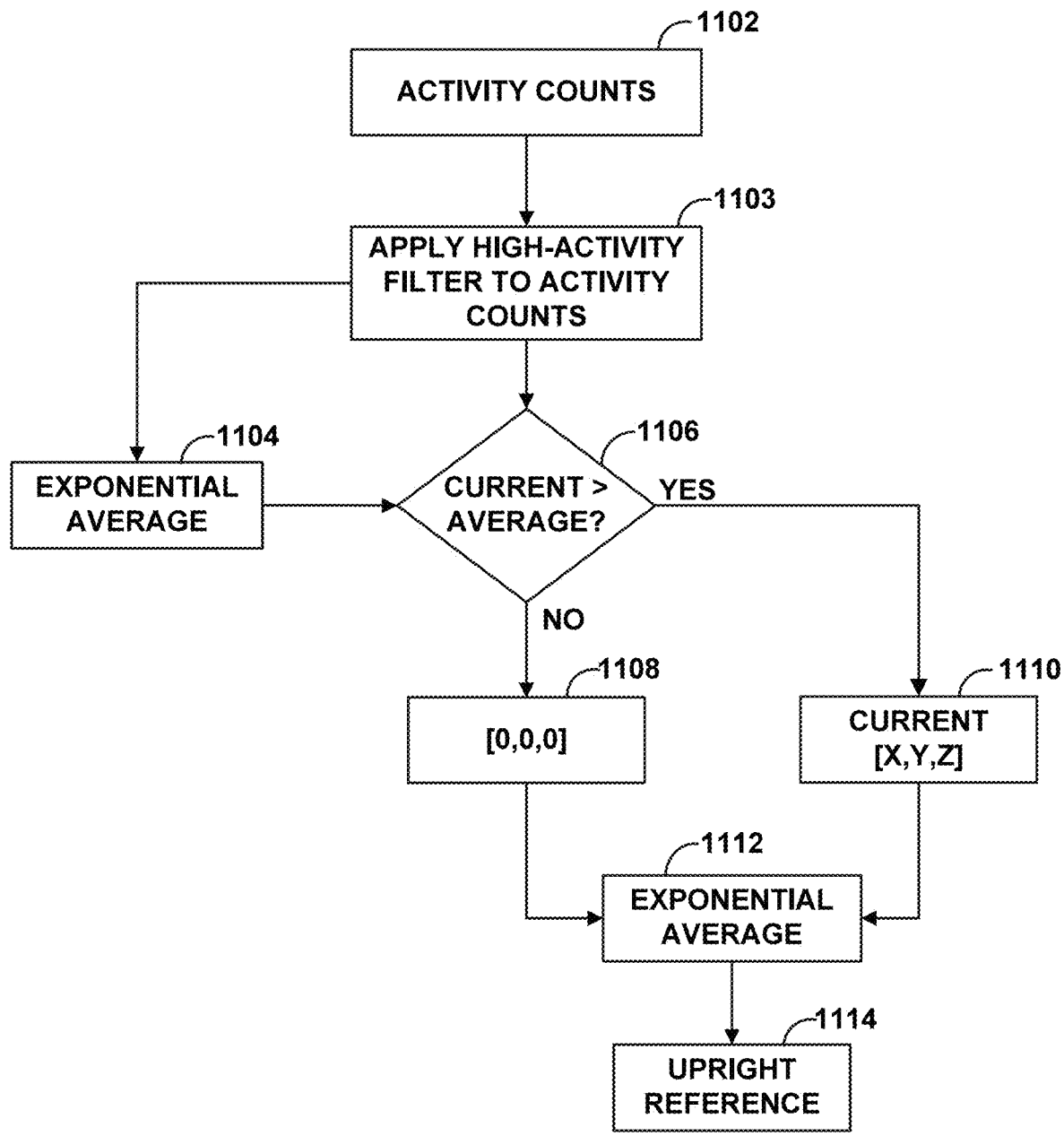
FIG. 11 is a flowchart illustrating an example operation in accordance with the techniques of the disclosure.

FIG. 11 is a flowchart illustrating an example operation in accordance with the techniques of the disclosure. For convenience, the operation of FIG. 10 is described with respect to IMD 10A of FIG. 1. However, the operation of FIG. 10 may be performed by other medical devices, such as IMD 10 of FIG. 2 or IMD 10B of FIGS. 5A-5C. Specifically, FIG. 11 illustrates an example operation for determining an upright vector of IMD 10. As described in more detail below, IMD 10A sets an activity threshold based on an average activity count for patient 2, determines, based on current activity counts, whether a sensed orientation vector should be incorporated into a subset of orientation vectors used for estimating the upright vector, and then estimates a current upright vector based on a moving average of the subset of orientation vectors that are coincident with periods of high activity of the patient.

IMD 10A determines an activity count for patient 2 (1102). An activity count may be used to indicate the activity or activity level of patient 2. For example, IMD 10A sums the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." When the activity count of patient 2 exceeds a first predetermined level, IMD 10A may determine that patient 2 has transitioned from a resting state to an active state.

In some examples, IMD 10A applies a high-activity filter to the activity count of patient 2 (1103). For example, IMD 10 may compare the current activity count of patient 2 with a second predetermined level. If the current activity count of patient 2 exceeds the second predetermined level, IMD 10 discards an orientation vector sensed concurrently for the time interval of the current activity count. In some examples, periods of high activity may be associated with artifacts. For example, high activity of patient 2, such as running, jumping, or climbing stairs, may exceed a maximum measurable limit of accelerometers of orientation and activity sensor 87, causing the accelerometers to saturate, or "rail." While the accelerometers are saturated due to high activity, values sensed by orientation and activity sensor 87 may be inaccurate or subject to error, leading to poor estimates of posture of patient 2. By rejecting orientation vectors sensed concurrently with activity counts indicative of periods of high activity of patient 2, IMD 10A may reduce error due to periods of high activity of patient 2. Therefore, IMD 10 may subsequently use only orientation vectors sensed concurrently with a "sweet" zone of activity levels for calculating the upright vector of patient 2 and/or the posture of patient 2.

IMD 10A further computes an exponential average of past activity counts of patient 2 (1104). IMD 10A compares the current activity count to the exponential average (1106). In response to determining that the current activity count is less than an exponential average of the activity count (e.g., "NO" block of 1106), IMD 10A discards an orientation vector sensed concurrently for the time interval of the current activity count (1108). In response to determining that the current activity count is greater than an exponential average of the activity count (e.g., "YES" block of 1106), IMD 10A includes an orientation vector sensed concurrently for the time interval of the current activity count (1110) in a subset of orientation vectors associated with an upright posture of patient 2.

IMD 10A is described as maintaining a subset of orientation vectors associated with the upright posture of patient 2 in the foregoing example. However, in other examples, IMD 10A may use infinite impulse response (IIR) filtering to estimate the upright vector. An IIR filter may only require a previous filter output (e.g., the moving average of previous orientation vectors associated with high activity of patient 2) and a current orientation vector to calculate the next output of the IIR filter (e.g., the updated upright vector). The use of an IIR filter may reduce the need for IMD 10A to store a large set of orientation vectors sensed for patient 2 to accurately estimate the upright vector.

IMD 10A computes an exponential average of the orientation vectors of the subset of orientation vectors associated with an upright posture of patient 2 (1112). IMD 10A may use the exponential average vector of the orientation vectors as the reference upright vector. In other words, IMD 10A may classify the reference upright vector as indicative of an upright posture of patient 2.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
sensing, by one or more sensors of an implantable medical device (IMD), a plurality of orientation vectors of the IMD with respect to a gravitational field;
clustering, by processing circuitry of the IMD, the plurality of orientation vectors into a first subset of orientation vectors;
defining, by the processing circuitry and based on the first subset of orientation vectors, an upright vector, the upright vector corresponding to an upright posture of a patient;
clustering, by the processing circuitry, the plurality of orientation vectors into a second subset of orientation vectors;
defining, by the processing circuitry and based on the second subset of orientation vectors and the upright vector, a transverse plane of the patient;
clustering, by the processing circuitry, the plurality of orientation vectors into a third subset of orientation vectors;
defining, by the processing circuitry and based on the third subset of orientation vectors and the upright vector, a sagittal plane of the patient; and
determining, by the processing circuitry and based on the upright vector, the transverse plane, and the sagittal plane, a reference orientation of the IMD.

2. The method of claim 1,
wherein sensing the plurality of orientation vectors comprises sensing the plurality of orientation vectors over a period of time,
wherein clustering the plurality of orientation vectors into the first subset of orientation vectors comprises determining one or more orientation vectors of the plurality of orientation vectors that correspond to an activity level of the patient that exceeds a patient activity threshold, and
wherein defining, based on the first subset of orientation vectors, the upright vector comprises averaging the one or more orientation vectors to compute the upright vector.

3. The method of claim 1,
wherein sensing the plurality of orientation vectors comprises sensing the plurality of orientation vectors over a period of time,
wherein clustering the plurality of orientation vectors into the first subset of orientation vectors comprises determining one or more orientation vectors of the plurality of orientation vectors that correspond to a walking activity of the patient, and
wherein defining, based on the first subset of orientation vectors, the upright vector comprises averaging the one or more orientation vectors to compute the upright vector.

4. The method of claim 1,
wherein sensing the plurality of orientation vectors comprises sensing the plurality of orientation vectors over a period of time,
wherein clustering the plurality of orientation vectors into the first subset of orientation vectors comprises:
receiving, from an external device, an indication of a posture of the patient for each of the plurality of orientation vectors;
determining, based on the indications of the posture of the patient, one or more orientation vectors of the plurality of orientation vectors that correspond to an upright posture of the patient, and
wherein defining, based on the first subset of orientation vectors, the upright vector comprises averaging the one or more orientation vectors to compute the upright vector.

5. The method of claim 1,
wherein clustering the plurality of orientation vectors into the second subset of orientation vectors comprises:
for each orientation vector of the plurality of orientation vectors:
determining an angle between the orientation vector and the upright vector;
comparing the angle between the orientation vector and the upright vector to a predetermined upright angle; and
classifying, based on the comparison, the orientation vector as one of the first subset of orientation vectors, the first subset of orientation vectors associated with the upright posture of the patient or one of the second subset of orientation vectors, the second subset of orientation vectors associated with a recumbent posture of the patient, and
wherein defining, based on the second subset of orientation vectors and the upright vector, the transverse plane of the patient comprises defining the transverse plane of the patient as a plane between the first subset of orientation vectors associated with the upright posture of the patient and the second subset of orientation vectors associated with the recumbent posture of the patient.

6. The method of claim 5, wherein clustering the orientation vector as one of the first subset of orientation vectors associated with the upright posture of the patient or one of the second subset of orientation vectors associated with the upright posture of the patient comprises:
- in response to determining that the angle between the orientation vector and the upright vector is less than the predetermined upright angle, classifying the orientation vector as one of the first subset of orientation vectors associated with the upright posture of the patient; and
- in response to determining that the angle between the orientation vector and the upright vector is greater than or equal to the predetermined upright angle, classifying the orientation vector as one of the second subset of orientation vectors associated with the recumbent posture of the patient.

7. The method of claim 1,
wherein clustering the plurality of orientation vectors into the third subset of orientation vectors comprises:
- associating each orientation vector of the plurality of orientation vectors with a grid element of a plurality of grid elements of a sphere based on an angle formed by the orientation vector and the upright vector;
- identifying a subset of the plurality of grid elements forming an angle with the upright vector that is less than a predetermined upright angle; and
- applying a clustering algorithm to identify a cluster of grid elements of the plurality of grid elements that are neighbors to the subset of the plurality of grid elements, wherein defining, based on the third subset of orientation vectors and the upright vector, the sagittal plane of the patient comprises:
- determining a main eigenvector for the cluster of grid elements, wherein the main eigenvector comprises a higher eigenvalue than each other eigenvector of a plurality of eigenvectors of the cluster of grid elements; and
- determining, based on the cross product of the upright vector with the main eigenvector, a normal vector, wherein the normal vector defines the sagittal plane of the patient.

8. The method of claim 1,
wherein the reference orientation of the IMD is a reference orientation of the IMD within the patient, and
wherein the method further comprises determining, based on the reference orientation of the IMD within the patient, a posture of the patient.

9. The method of claim 8, wherein determining the posture of the patient comprises:
- sensing, by the one or more sensors of an IMD, a current orientation vector of the patient with respect to the gravitational field; and
- determining, by the processing circuitry and based on a relationship of the current orientation vector to the reference orientation of the IMD, the posture of the patient.

10. The method of claim 1, wherein the defined transverse plane of the patient is not substantially perpendicular to the defined sagittal plane of the patient.

11. The method of claim 1, wherein clustering the plurality of orientation vectors into the first subset of orientation vectors comprises:
- determining at least one orientation vector of the plurality of orientation vectors that is concurrent with a high activity level of the patient; and
- rejecting the at least one orientation vector to identify the upright vector of the plurality of orientation vectors.

12. The method of claim 1, wherein sensing the plurality of orientation vectors of the IMD comprises sensing the plurality of orientation vectors of the IMD while the patient is in a plurality of different postures.

13. The method of claim 1, wherein sensing the plurality of orientation vectors of the IMD comprises sensing the plurality of orientation vectors of the IMD during both a period of activity of the patient and a period of inactivity of the patient.

14. The method of claim 1,
wherein sensing the plurality of orientation vectors comprises sensing the plurality of orientation vectors over a period of time, and
wherein defining, based on the first subset of orientation vectors, the upright vector comprises defining the upright vector based on a moving average of the first subset of orientation vectors with respect to the period of time.

15. An implantable medical device (IMD) comprising:
one or more sensors configured to sense a plurality of orientation vectors of the IMD with respect to a gravitational field; and
processing circuitry configured to:
- cluster the plurality of orientation vectors into a first subset of orientation vectors;
- define, based on the first subset of orientation vectors, an upright vector, the upright vector corresponding to an upright posture of a patient;
- cluster the plurality of orientation vectors into a second subset of orientation vectors;
- define, based on the second subset of orientation vectors and the upright vector, a transverse plane of the patient;
- cluster the plurality of orientation vectors into a third subset of orientation vectors;
- define, based on the third subset of orientation vectors and the upright vector, a sagittal plane of the patient; and
- determine, based on the upright vector, the transverse plane, and the sagittal plane, a reference orientation of the IMD.

16. The IMD of claim 15,
wherein the processing circuitry is configured to sense the plurality of orientation vectors over a period of time,
wherein to cluster the plurality of orientation vectors into the first subset of orientation vectors, the processing circuitry is configured to determine one or more orientation vectors of the plurality of orientation vectors that correspond to an activity level of the patient that exceeds a patient activity threshold, and
wherein to define, based on the first subset of orientation vectors, the upright vector, the processing circuitry is configured to average the one or more orientation vectors to compute the upright vector.

17. The IMD of claim 15,
wherein the processing circuitry is configured to sense the plurality of orientation vectors over a period of time,
wherein to cluster the plurality of orientation vectors into the first subset of orientation vectors, the processing circuitry is configured to determine one or more orientation vectors of the plurality of orientation vectors that correspond to a walking activity of the patient, and
wherein to define, based on the first subset of orientation vectors, the upright vector, the processing circuitry is configured to average the one or more orientation vectors to compute the upright vector.

18. The IMD of claim 15, wherein to cluster the plurality of orientation vectors into the second subset of orientation vectors, the processing circuitry is configured to:
 for each orientation vector of the plurality of orientation vectors:
  determine an angle between the orientation vector and the upright vector;
  compare the angle between the orientation vector and the upright vector to a predetermined upright angle; and
  classify, based on the comparison, the orientation vector as one of the first subset of orientation vectors, the first subset of orientation vectors associated with the upright posture of the patient or one of the second subset of orientation vectors, the second subset of orientation vectors associated with a recumbent posture of the patient, and
 wherein to define, based on the second subset of orientation vectors and the upright vector, the transverse plane of the patient, the processing circuitry is configured to define the transverse plane of the patient as a plane between the first subset of orientation vectors associated with the upright posture of the patient and the second subset of orientation vectors associated with the recumbent posture of the patient.

19. The IMD of claim 15,
 wherein the reference orientation of the IMD is a reference orientation of the IMD within the patient, and
 wherein the processing circuitry is further configured to determine, based on the reference orientation of the IMD within the patient, a posture of the patient.

20. The IMD of claim 19, wherein to determine the posture of the patient, the processing circuitry is configured to:
 sense, by the one or more sensors of an IMD, a current orientation vector of the patient with respect to the gravitational field; and
 determine, by the processing circuitry and based on a relationship of the current orientation vector to the reference orientation of the IMD, the posture of the patient.

21. A system comprising:
 one or more sensors configured to sense a plurality of orientation vectors of an implantable medical device (IMD) with respect to a gravitational field; and
 processing circuitry configured to:
  cluster the plurality of orientation vectors into a first subset of orientation vectors;
  define, based on the first subset of orientation vectors, an upright vector, the upright vector corresponding to an upright posture of a patient;
  cluster the plurality of orientation vectors into a second subset of orientation vectors;
  define, based on the second subset of orientation vectors and the upright vector, a transverse plane of the patient;
  cluster classify the plurality of orientation vectors with respect to the upright vector into a third subset of orientation vectors;
  define, based on the third subset of orientation vectors and the upright vector, a sagittal plane of the patient; and
  determine, based on the upright vector, the transverse plane, and the sagittal plane, a reference orientation of the IMD.

22. The system of claim 21, wherein the IMD comprises the processing circuitry.

23. The system of claim 21, wherein an external medical device comprises the processing circuitry.

* * * * *